(12) United States Patent
Esch et al.

(10) Patent No.: US 6,440,124 B1
(45) Date of Patent: Aug. 27, 2002

(54) FLEXIBLE FLOW APPARATUS AND METHOD FOR THE DISRUPTION OF OCCLUSIONS

(75) Inventors: Victor C. Esch, Albuquerque, NM (US); Paul S. Jackson, Redwood City, CA (US)

(73) Assignee: Endovasix, Inc., Belmont, CA (US)

( * ) Notice: Subject to any disclaimer, the term of this patent is extended or adjusted under 35 U.S.C. 154(b) by 22 days.

(21) Appl. No.: 09/676,131

(22) Filed: Sep. 29, 2000

Related U.S. Application Data

(63) Continuation-in-part of application No. 09/328,514, filed on Jun. 9, 1999, which is a continuation-in-part of application No. 09/165,435, filed on Oct. 2, 1998, now Pat. No. 6,210,400, which is a continuation-in-part of application No. 09/120,598, filed on Jul. 22, 1998, now Pat. No. 6,139,543.

(51) Int. Cl.[7] ................................................ A61B 18/18
(52) U.S. Cl. ................................ 606/7; 606/15; 606/16
(58) Field of Search ........................ 606/3, 7, 8, 13–16; 128/898; 604/892.1, 10, 22, 48; 607/89

(56) References Cited

U.S. PATENT DOCUMENTS

| | | |
|---|---|---|
| 4,587,972 A | 5/1986 | Morantte |
| 4,685,458 A | 8/1987 | Leckrone |
| 4,739,768 A | 4/1988 | Engelson |
| 4,747,405 A | 5/1988 | Leckrone |
| 4,781,681 A | 11/1988 | Sharrow et al. |
| 4,784,132 A | 11/1988 | Fox et al. |
| 4,878,492 A | 11/1989 | Sinofsky et al. |
| 5,026,367 A | 6/1991 | Leckrone et al. |
| 5,041,108 A | 8/1991 | Fox et al. |
| 5,095,915 A | 3/1992 | Engelson |
| 5,109,859 A | 5/1992 | Jenkins |
| 5,116,227 A | 5/1992 | Levy |
| 5,207,988 A | 5/1993 | Lucas |

(List continued on next page.)

FOREIGN PATENT DOCUMENTS

| | | |
|---|---|---|
| DE | 3840126 A | 5/1990 |
| EP | 0571306 A | 11/1993 |
| WO | WO 9110403 A | 7/1991 |
| WO | WO 9920189 | 4/1999 |
| WO | WO 0003292 | 1/2000 |

OTHER PUBLICATIONS

Written Opinion of International Application No. PCT/US99/16371.

Yuan, H. and Prosperetti, A. (1997) "Gas–liquid Heat Transfer in a Bubble Collapsing Near a Wall," *Phys. Fluids* 9(1):127–142.

(List continued on next page.)

*Primary Examiner*—John Mulcahy
*Assistant Examiner*—Ahmed Farah
(74) *Attorney, Agent, or Firm*—Skjerven Morrill LLP; K. Alison de Runtz

(57) ABSTRACT

The invention encompasses methods and flexible apparatus for delivering radiation energy to a radiation-absorbing fluid within the apparatus to generate a series of expanding and collapsing bubbles therein, and thereby generate flow in a fluid surrounding the apparatus. Effective fluid flow is obtained via at least one optical fiber, disposed within the apparatus near a distal opening therein, that, when fired, tends to pump fluid with respect to the apparatus, and at least one other optical fiber, disposed within the apparatus in the vicinity of a side opening thereof, that, when fired, tends to agitate fluid near its distal end. These pumping and agitative actions cause a net fluid motion that is particularly effective in disrupting a partial or total occlusion in a body passage, such as a blood vessel, within which the apparatus is operated. While a relatively low level of radiation energy or power may be used for such applications, it may be desirable to increase the radiation energy or power to obtain greater disruption effects. The apparatus is adapted to provide a cooling medium to the body passage to avoid causing any substantial thermal injury to the walls of the passage, particularly when the apparatus is operated using the higher power levels within a suitable power range.

38 Claims, 19 Drawing Sheets

U.S. PATENT DOCUMENTS

| | | | |
|---|---|---|---|
| 5,304,171 | A | | 4/1994 Gregory et al. |
| 5,312,356 | A | | 5/1994 Engelson et al. |
| 5,370,617 | A | | 12/1994 Sahota |
| 5,397,301 | A | * | 3/1995 Pflueger et al. ............... 604/22 |
| 5,417,653 | A | | 5/1995 Sahota et al. |
| 5,437,659 | A | | 8/1995 Leckrone |
| B24,739,768 | A | | 10/1995 Engelson |
| 5,472,406 | A | | 12/1995 de la Torre et al. |
| 5,500,012 | A | | 3/1996 Brucker et al. |
| 5,571,169 | A | | 11/1996 Plaia et al. |
| 5,599,492 | A | | 2/1997 Engelson |
| 5,649,923 | A | | 7/1997 Gregory et al. |
| 5,662,590 | A | | 9/1997 de la Torre et al. |
| 5,688,234 | A | * | 11/1997 Frisbie ........................ 604/22 |
| 5,722,972 | A | | 3/1998 Power et al. |
| 5,746,709 | A | | 5/1998 Rom et al. |
| 5,776,127 | A | | 7/1998 Anderson et al. |
| 5,817,144 | A | | 10/1998 Gregory |
| 5,833,682 | A | | 11/1998 Amplatz et al. |
| 5,944,687 | A | | 8/1999 Benett et al. |
| 5,964,751 | A | | 10/1999 Amplatz et al. |
| 5,989,243 | A | | 11/1999 Goldenberg |
| 6,022,309 | A | | 2/2000 Celliers et al. |
| 6,024,738 | A | | 2/2000 Daikuzono et al. |
| 6,033,371 | A | | 3/2000 de la Torre et al. |
| 6,056,743 | A | | 5/2000 Ellis et al. |
| 6,066,130 | A | | 5/2000 Gregory et al. |
| 6,102,905 | A | | 8/2000 Baxter et al. |
| 6,106,546 | A | | 8/2000 Gregory |
| 6,139,543 | A | | 10/2000 Esch et al. |
| 6,156,029 | A | | 12/2000 Mueller |
| 6,156,032 | A | * | 12/2000 Lennox ....................... 606/41 |
| 6,200,307 | B1 | | 3/2001 Kasinkas et al. |
| 6,210,400 | B1 | | 4/2001 Hebert et al. |
| 6,295,990 | B1 | * | 10/2001 Lewis et al. ................ 128/898 |

OTHER PUBLICATIONS

Brujan, E.A. et al. (1996) "Dynamics of Laser–Induced Cavitation Bubbles in Polymer Solutions," *ACUSTICA acta acustica* 82:423–430.

Hao, Y. and Prosperetti, A. (1999) "The Dynamics of Vapor Bubbles in Acoustic Pressure Fields," *Physics of Fluids* 11(8):2008–2019.

Jun, Thomas K. and Kim, Chang–Jin (1996) "Microscale Pumping with traversing Bubbles in Microchannels," *Solid–State Sensor and Actuator Workshop*, Hilton Head, South Carolina pp. 144–147.

Oguz, H.N. and Prosperetti, A. (1998) "The Natural Frequency of Oscillation of gas Bubbles in Tubes," *J. Acoust. Soc. Am.* 103:3301–3308.

Yuan, H. et al. (1999) "Growth and Collapse of a Vapor Bubble in a Small Tube," *International Journal of Heat and Mass Transfer* 42:3643–3657.

Brookshier, K.A. et al. (1993) "Evaluation of a Transparent Blood Analog Fluid: Aqueous Xanthan Gum/Glycerin," *Biorheology* 30:107–116.

Brujan, E.A. et al. (1996) "Dynamics of Laser–Induced Cavitation Bubbles in Polymer Solutions," *ACUSTICA acta acustica* 82:423–430.

Hao, Y. et al., A. (1999) "The Dynamics of Vapor Bubbles in Acoustic Pressure Fields," *Physics of Fluids* 11(8):2008–2019.

Jun, Thomas K. et al. (1996) "Microsale Pumping with Traversing Bubbles in Microchannels," *Solid–State Sensor and Actuator Workshop*, Hilton Head, South Carolina pp. 144–147.

Oguz, H.N. et al. (1998) "The Natural Frequency of Oscillation of Gas Bubbles in Tubes," *J. Acoust. Soc. Am.* 103:3301–3308.

Yuan, H. et al. (1997) "Gas–Liquid Heat Transfer in a Bubble Collapsing Near a Wall," *Phys. Fluids* 9(1):127–142.

Yuan, H. et al. (1999) "Growth and Collapse of a Vapor Bubble in a Small Tube," *International Journal of Heat and Mass Transfer* 42:3643–3657.

* cited by examiner

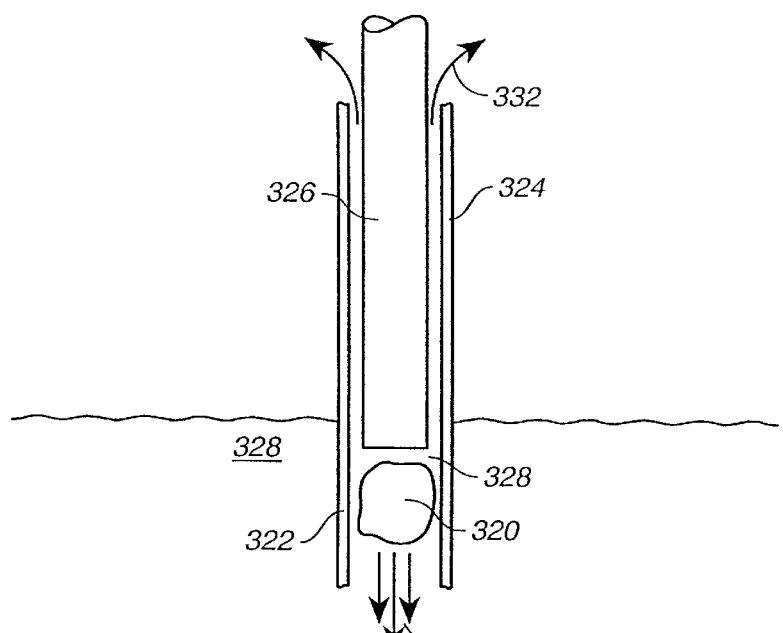
FIG._1 EXPANSION DIRECTION OF BUBBLE
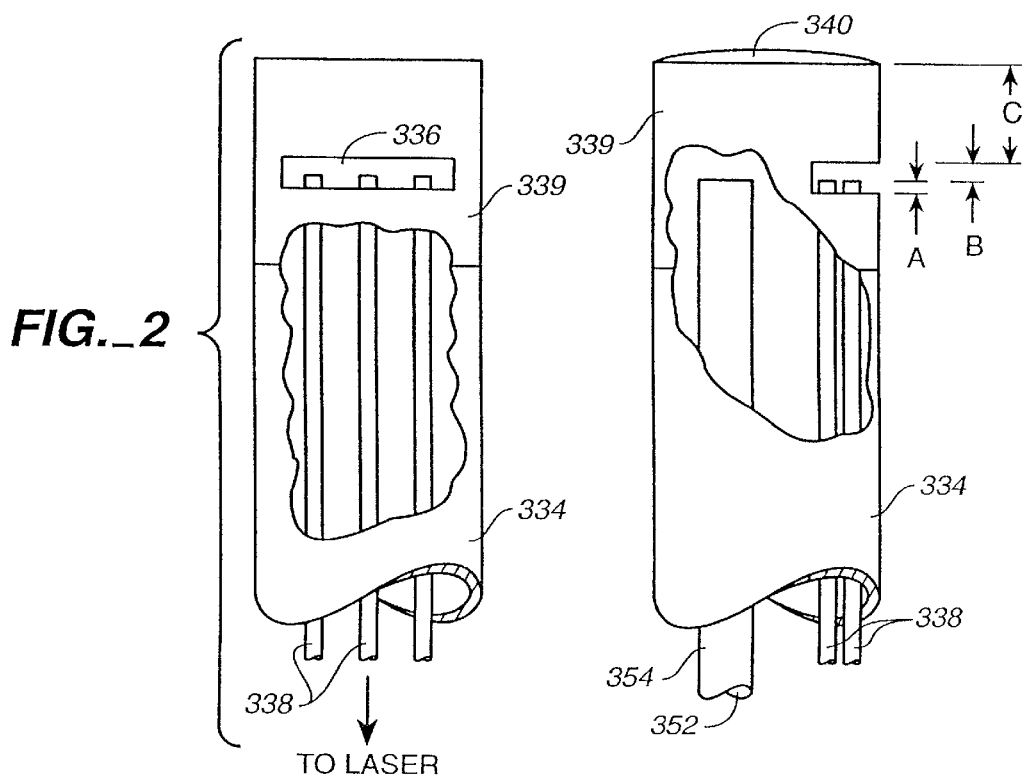
FIG._2

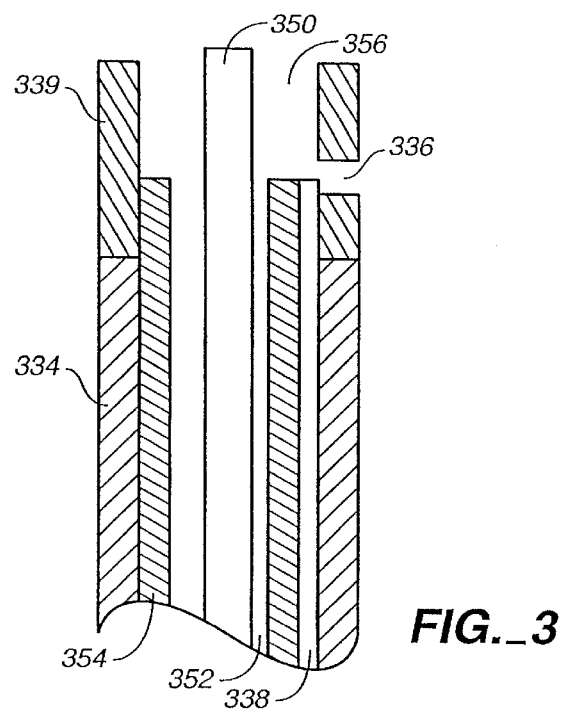
FIG._3
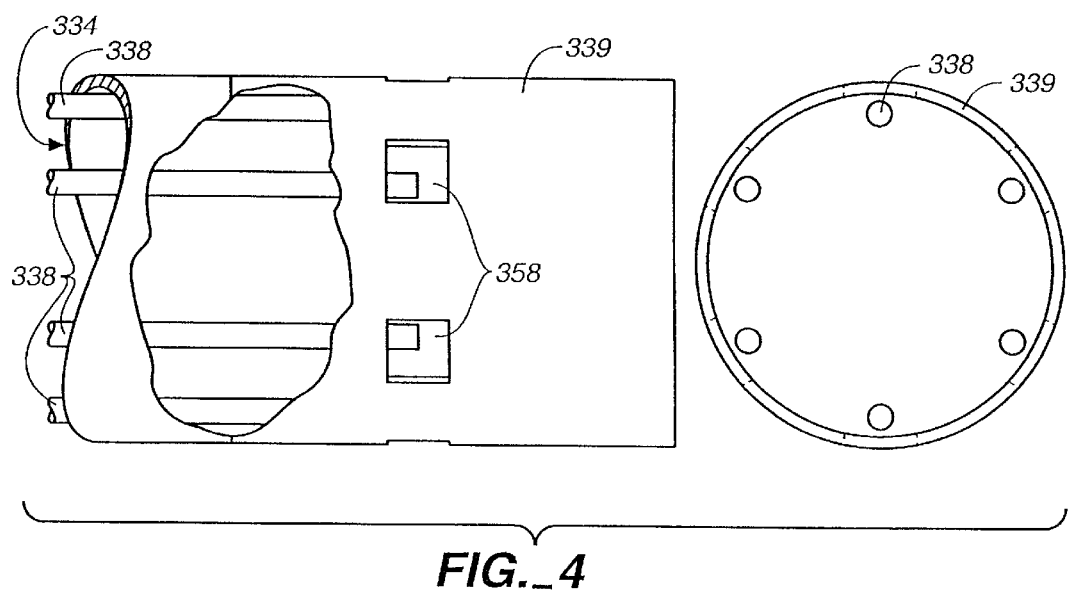
FIG._4

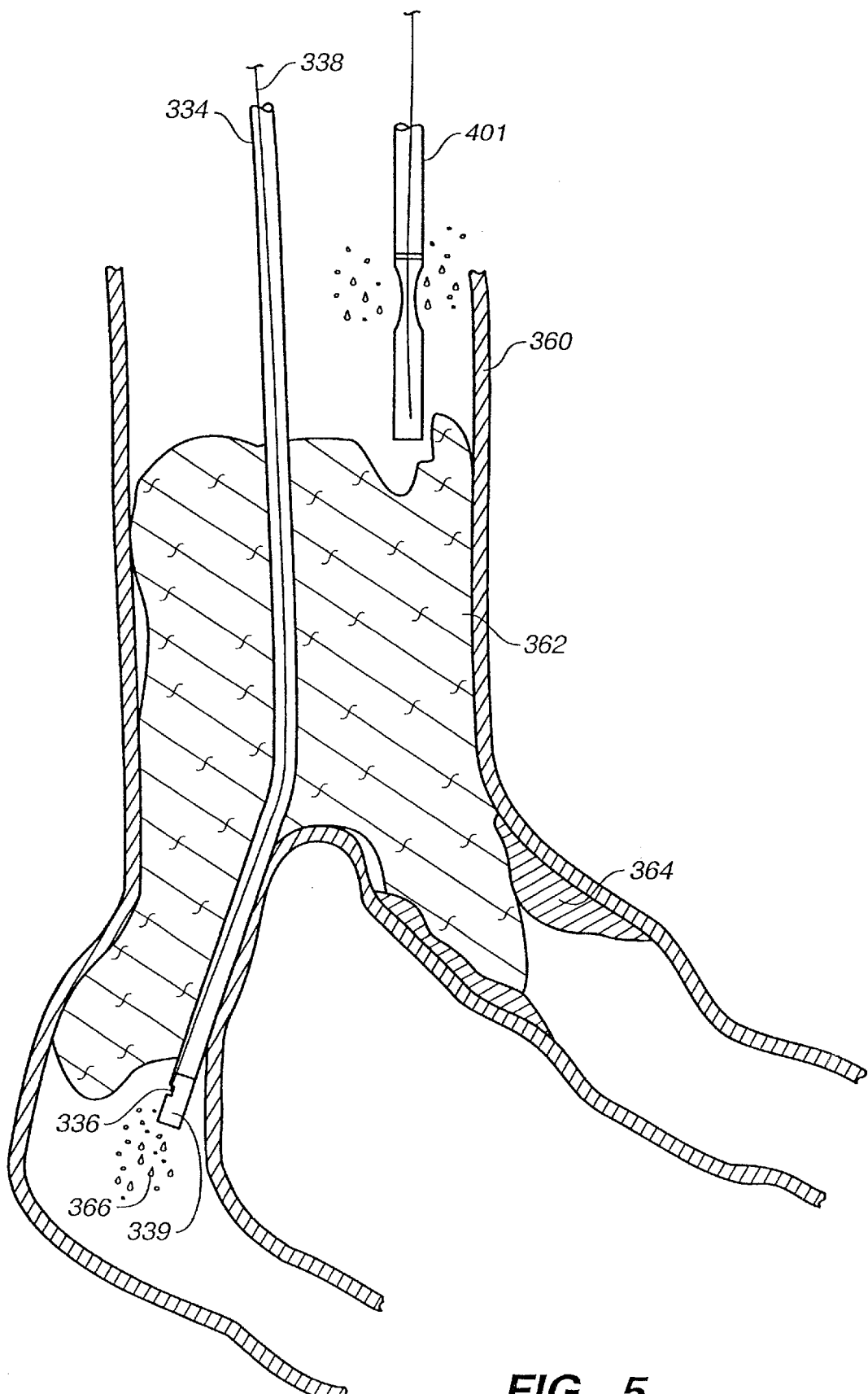
FIG._5

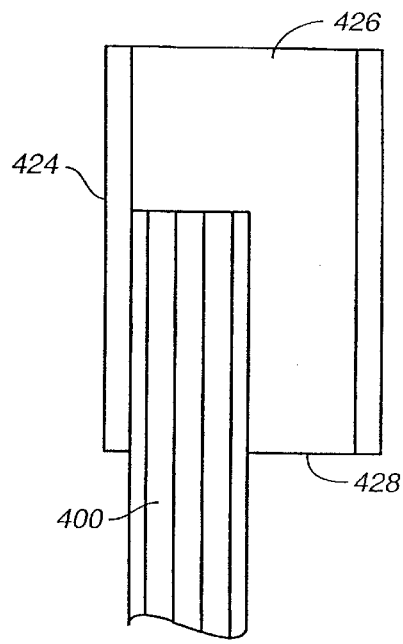
FIG._6
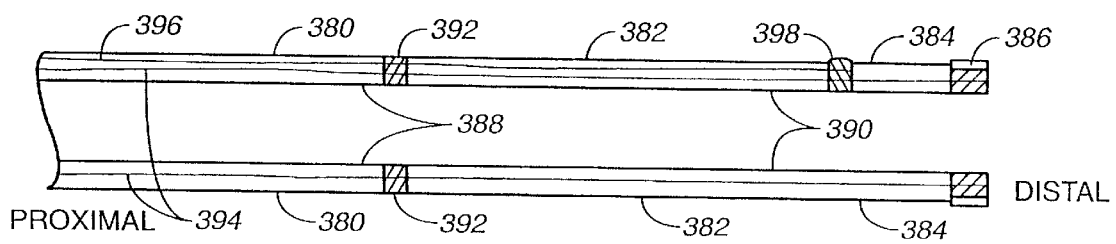
FIG._7A

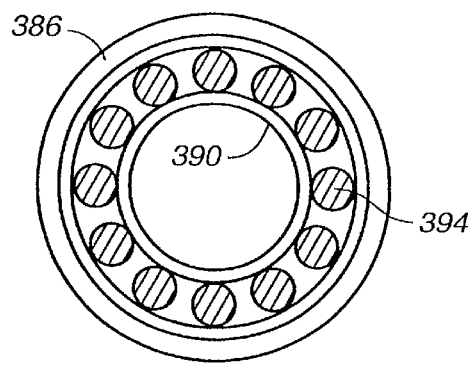
FIG._7B
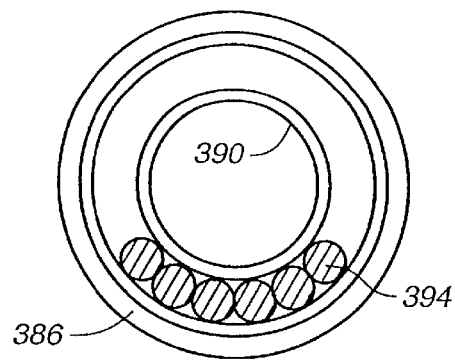
FIG._7C
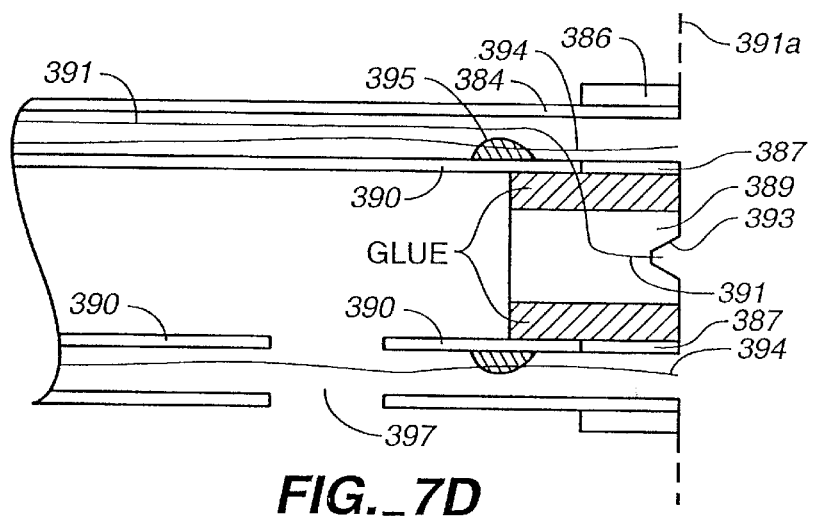
FIG._7D
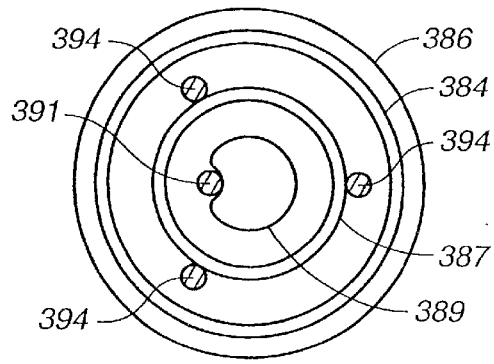
FIG._7E

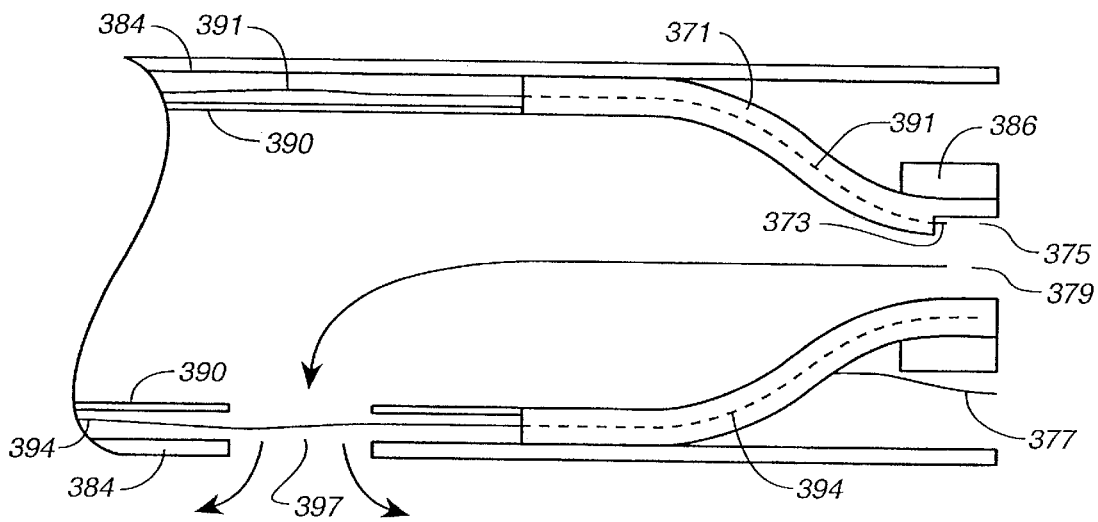
FIG._8A
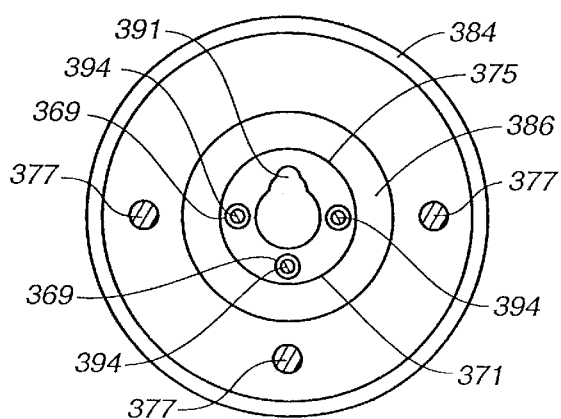
FIG._8B

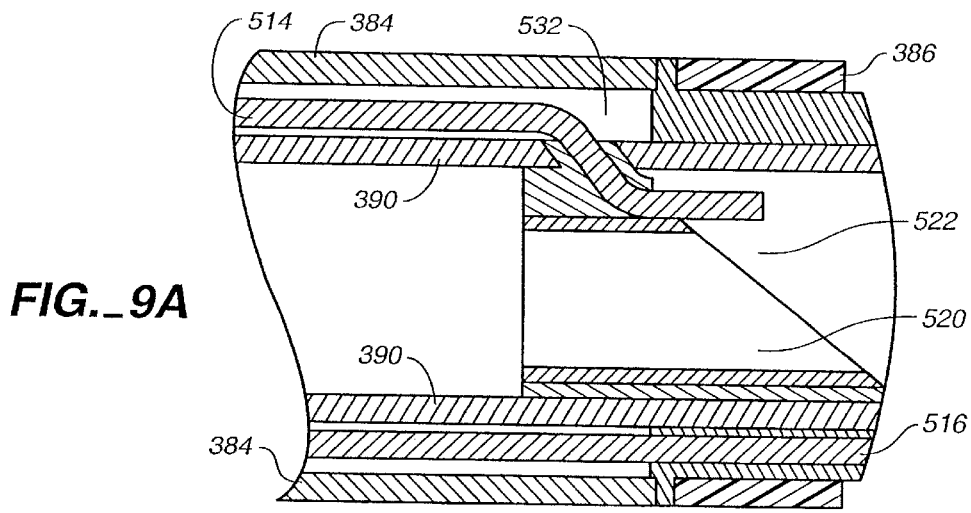
FIG._9A
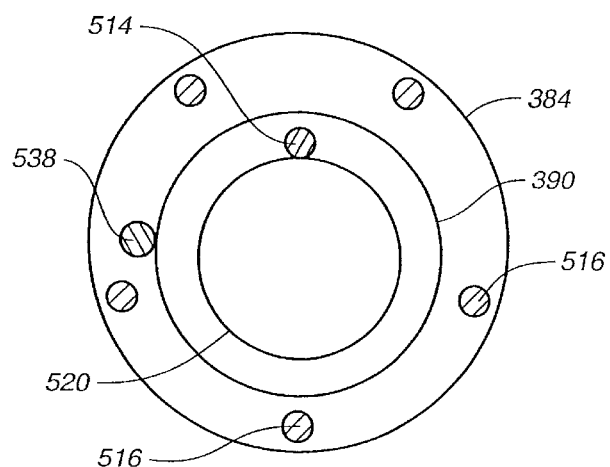
FIG._9B
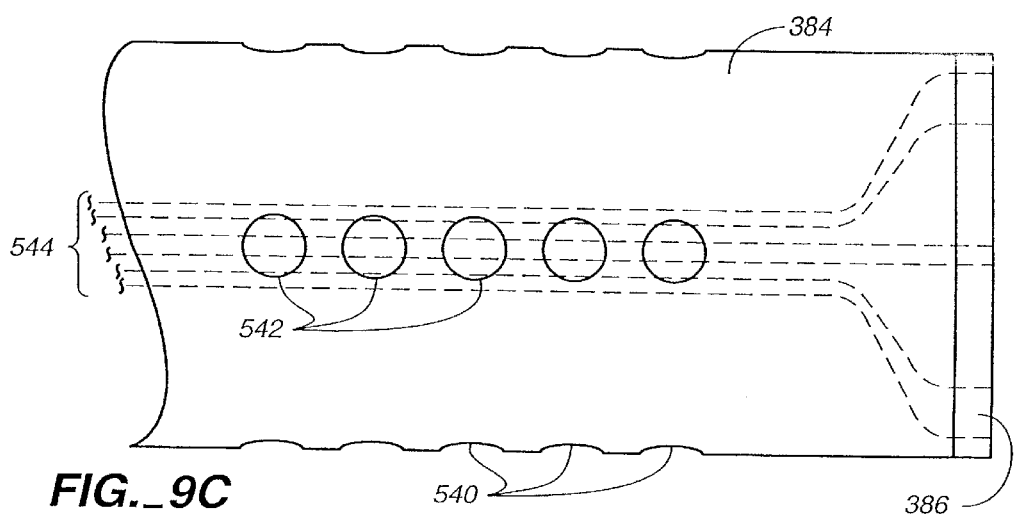
FIG._9C

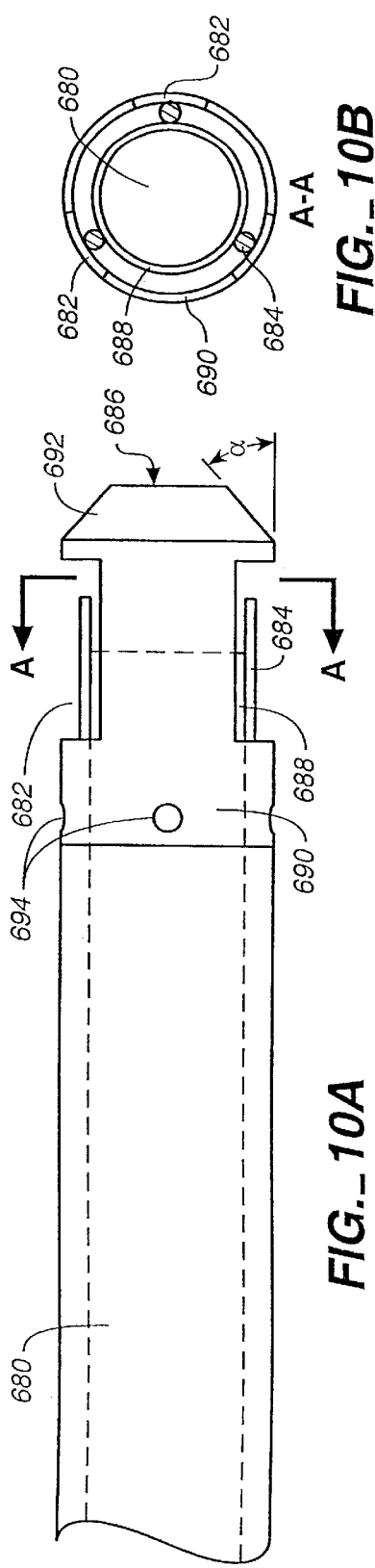
FIG._10A
FIG._10B
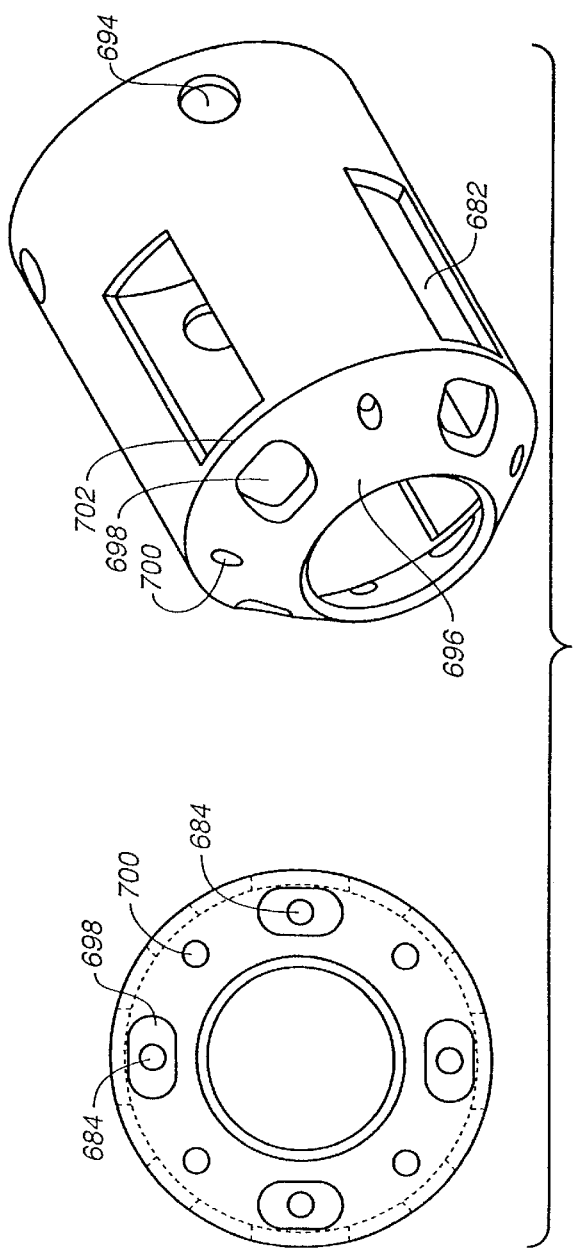
FIG._11

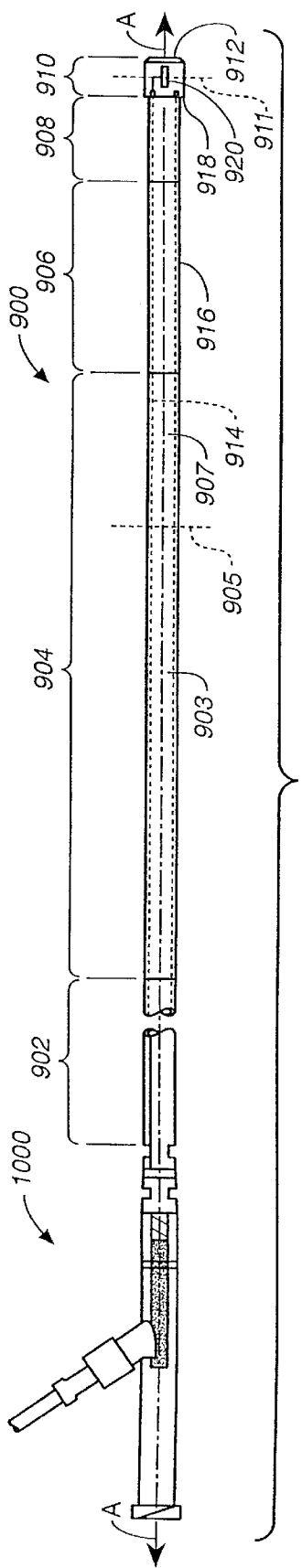
FIG._12A
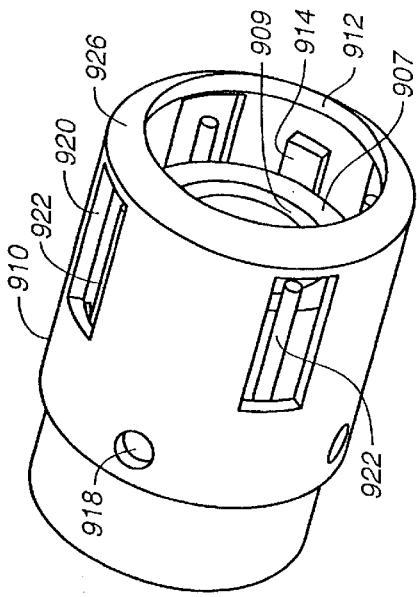
FIG._12C
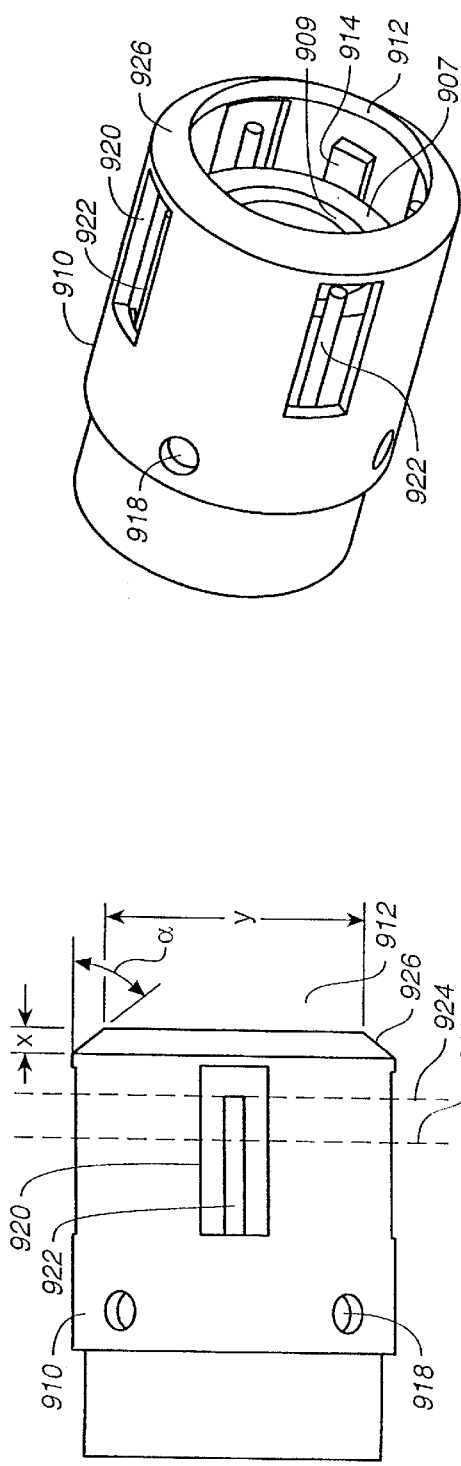
FIG._12B

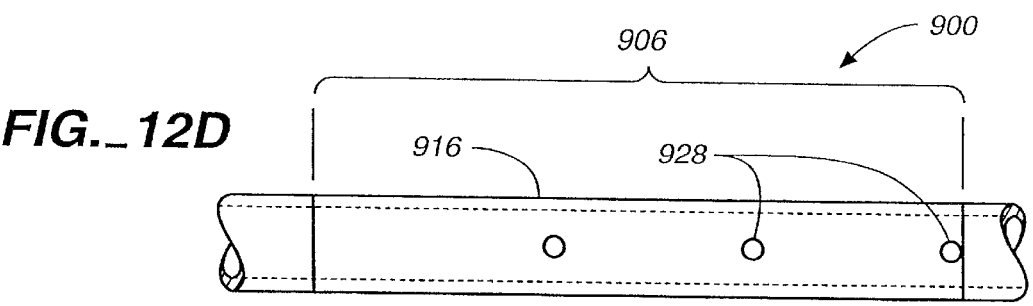
FIG._12D
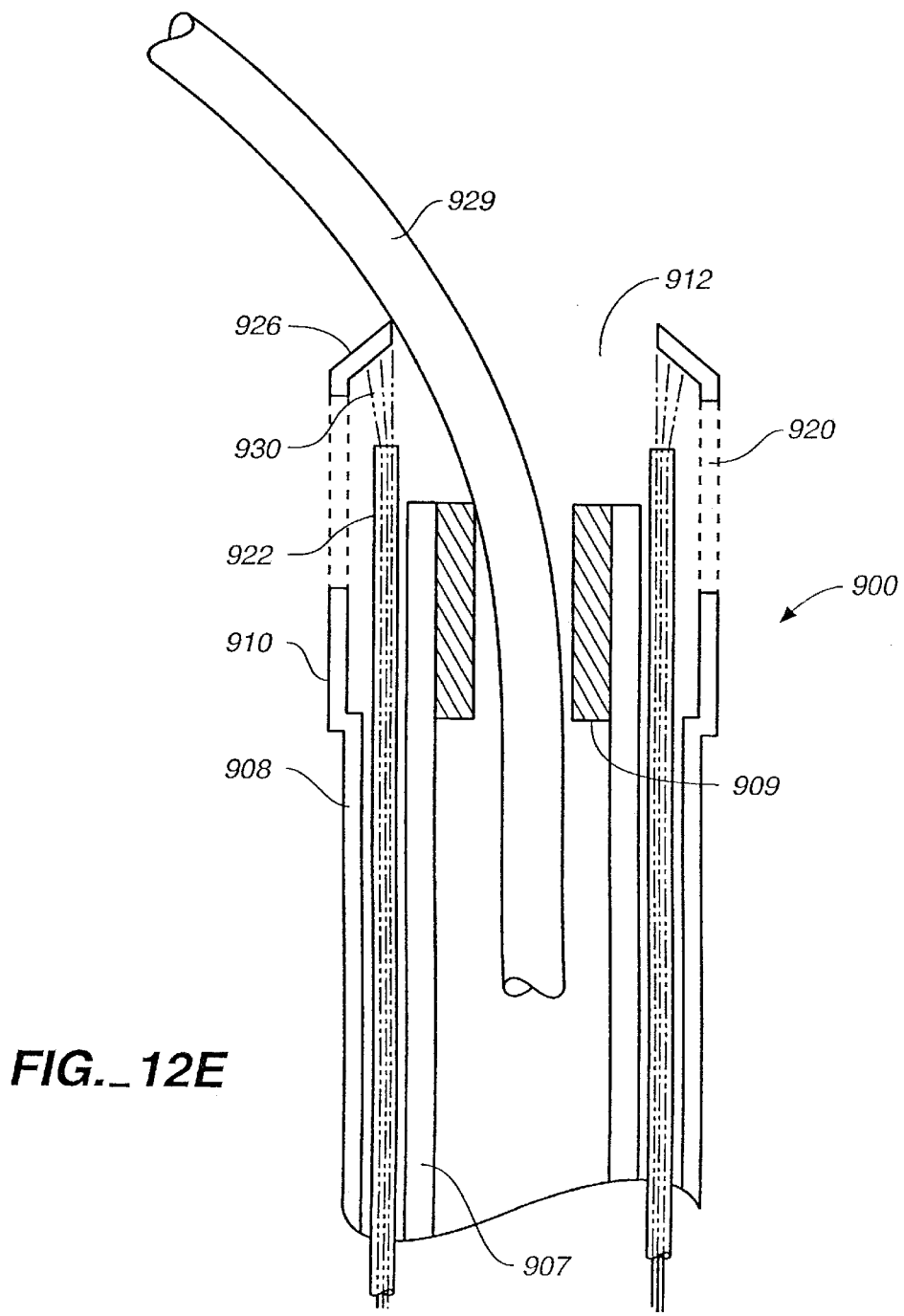
FIG._12E

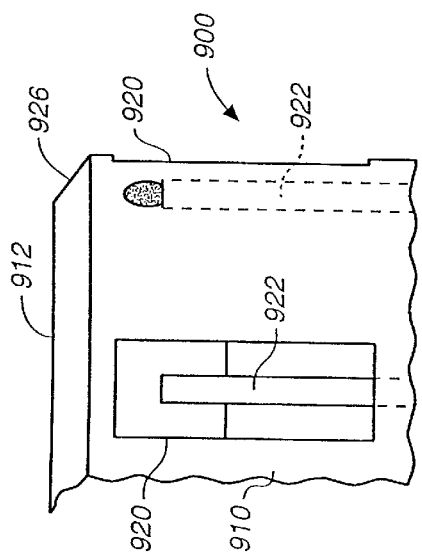
FIG._13A
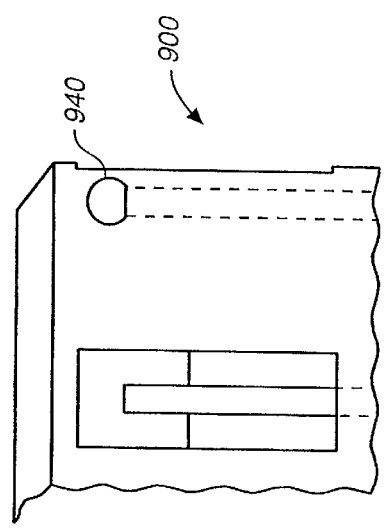
FIG._13B
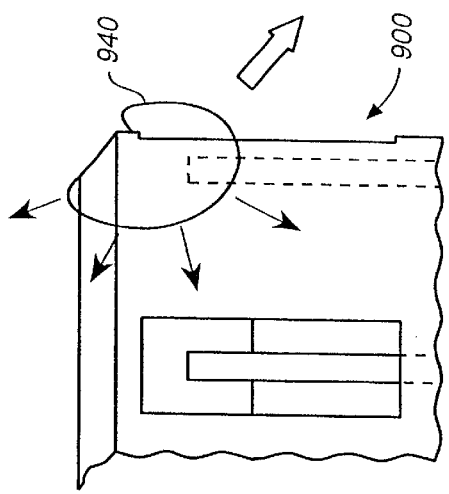
FIG._13C
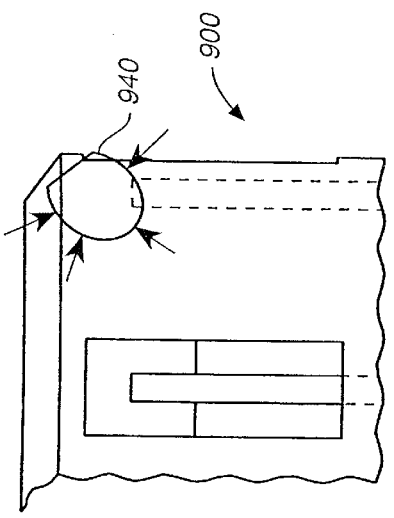
FIG._13D
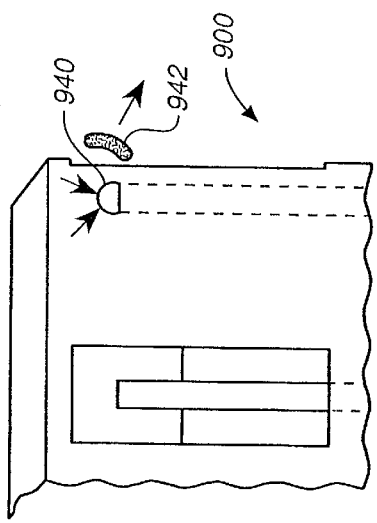
FIG._13E
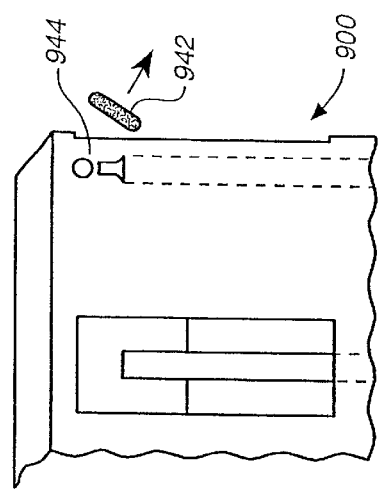
FIG._13F

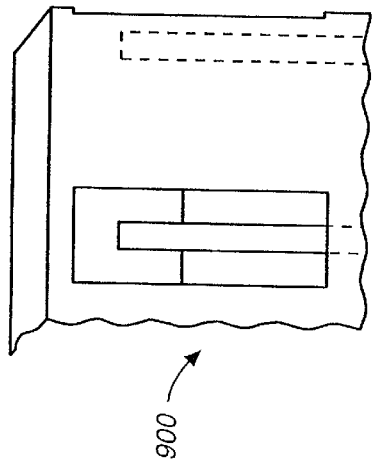
FIG._14B
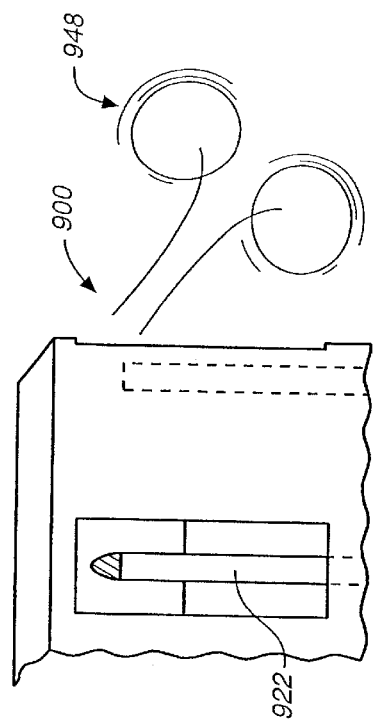
FIG._14D
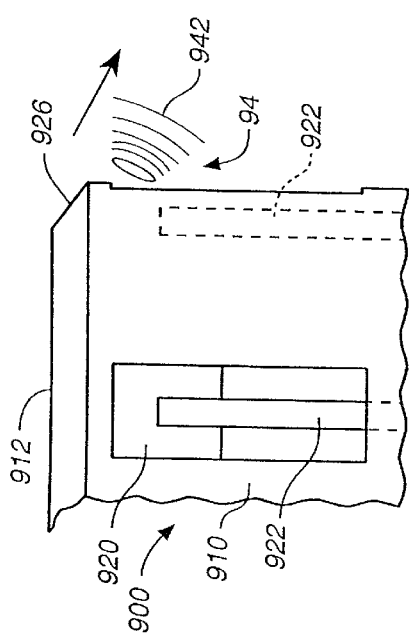
FIG._14A
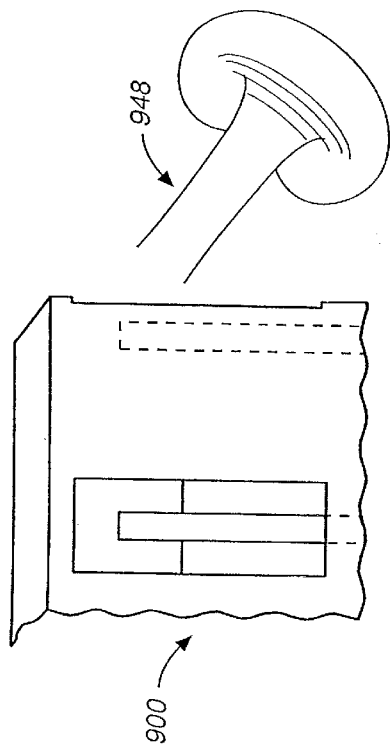
FIG._14C

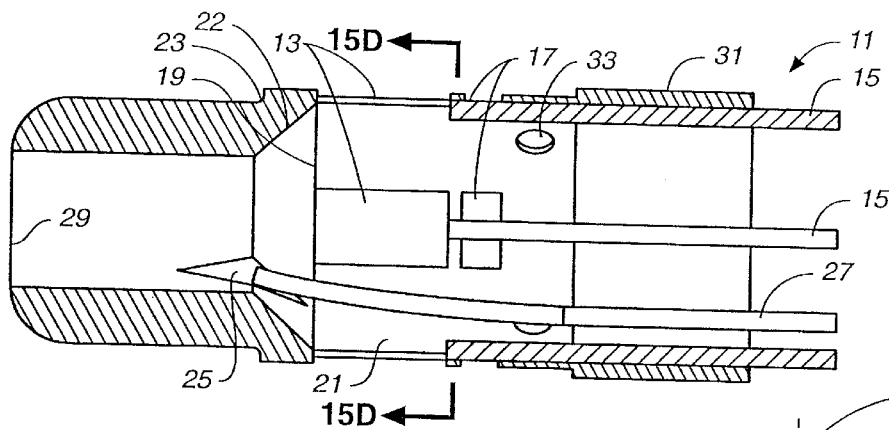
FIG._15A
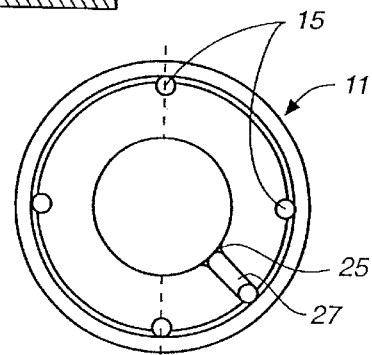
FIG._15D
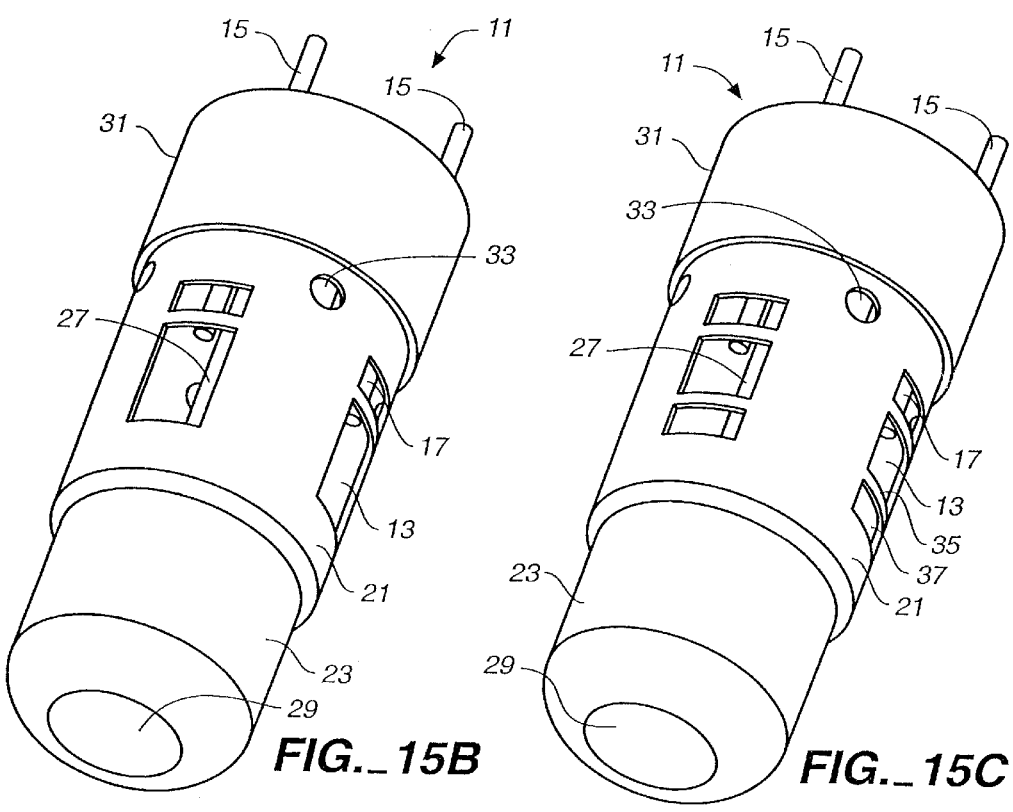
FIG._15B     FIG._15C

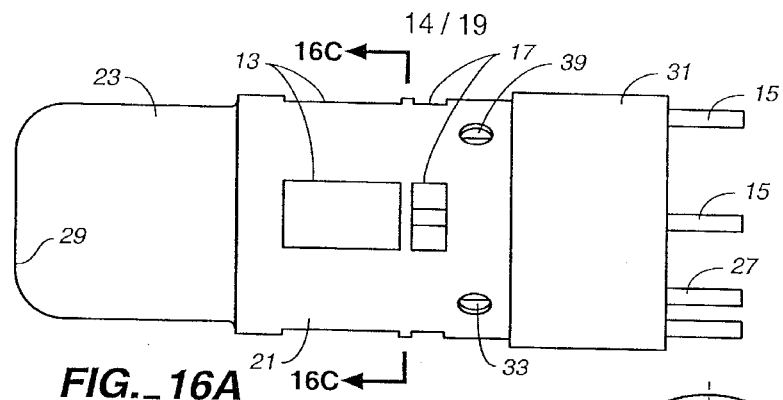

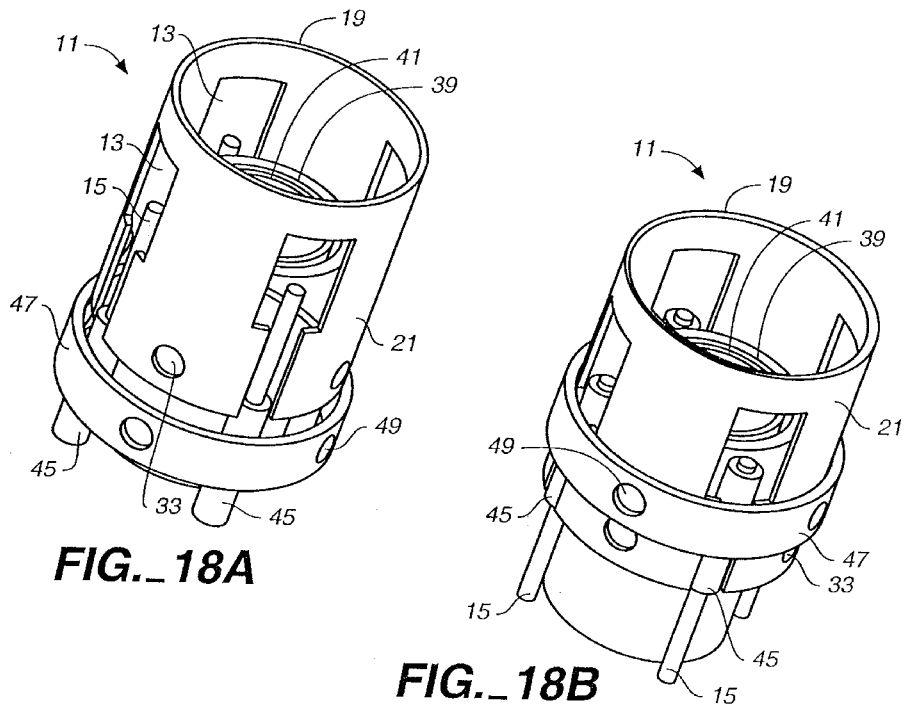
FIG._18A
FIG._18B
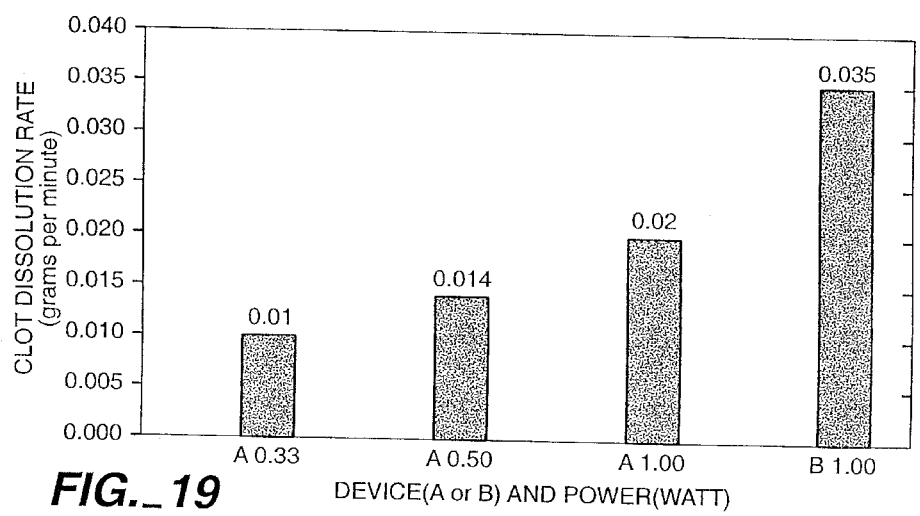
FIG._19

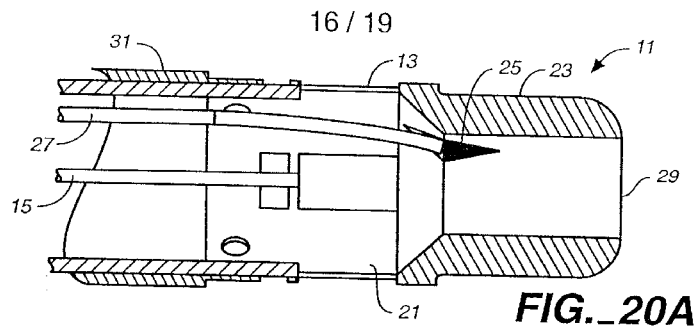
FIG._20A
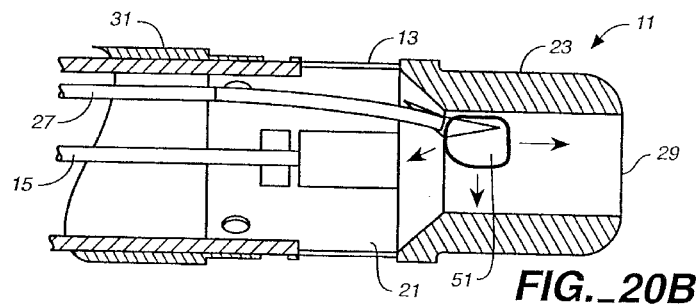
FIG._20B
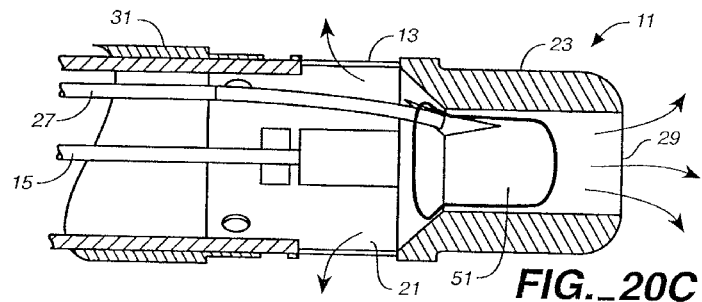
FIG._20C
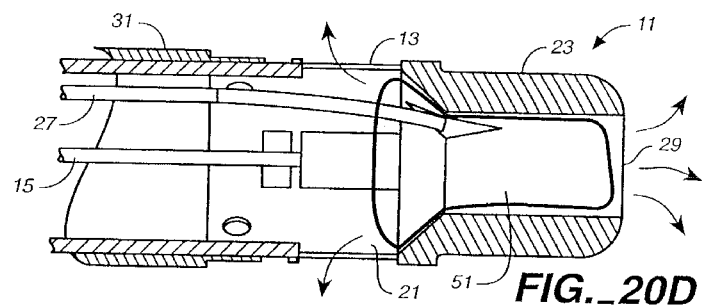
FIG._20D

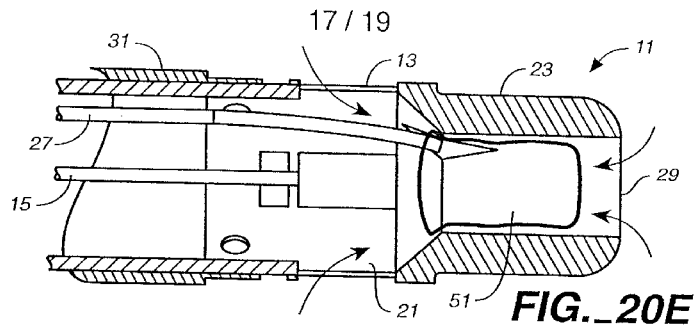
FIG._20E
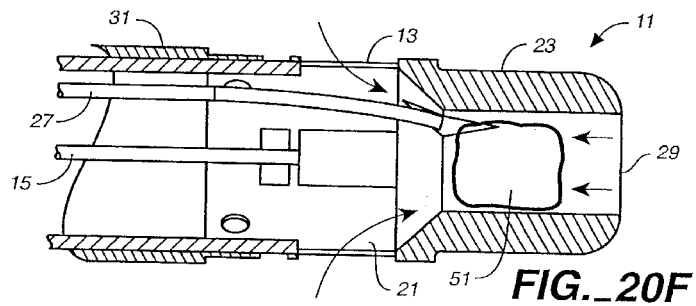
FIG._20F
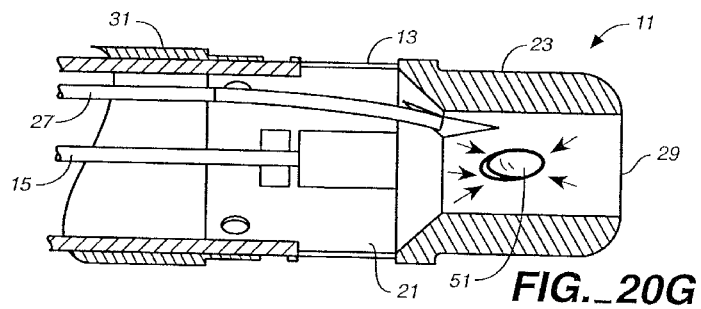
FIG._20G
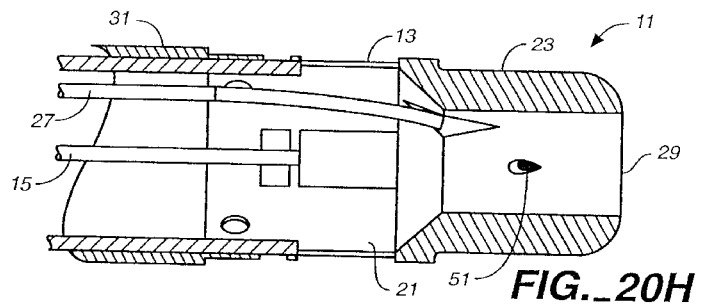
FIG._20H

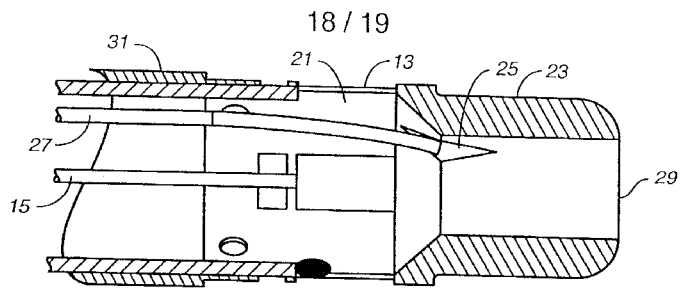
FIG._21A
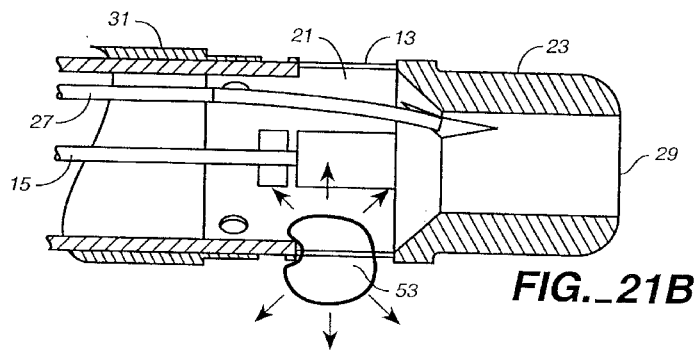
FIG._21B
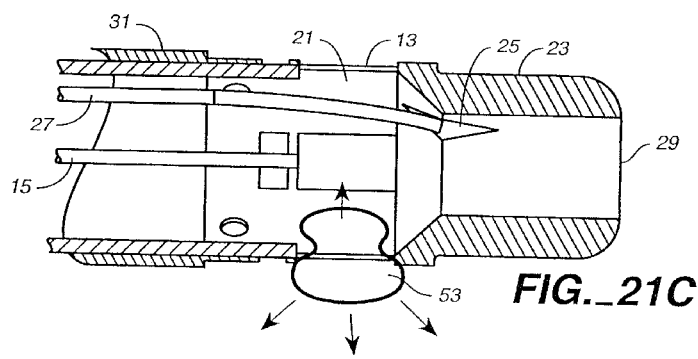
FIG._21C
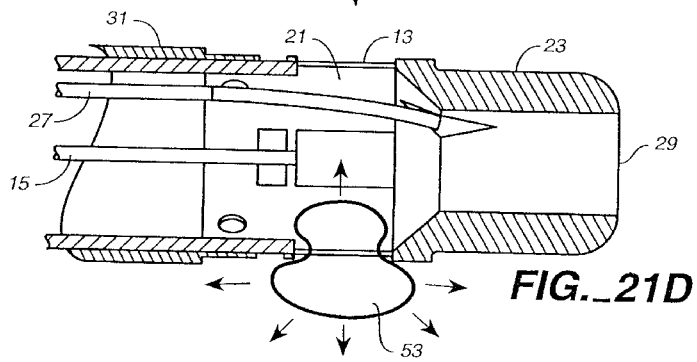
FIG._21D

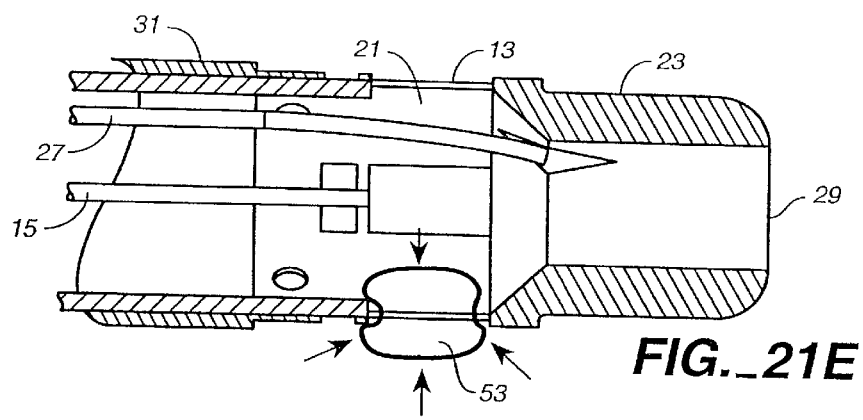
FIG._21E
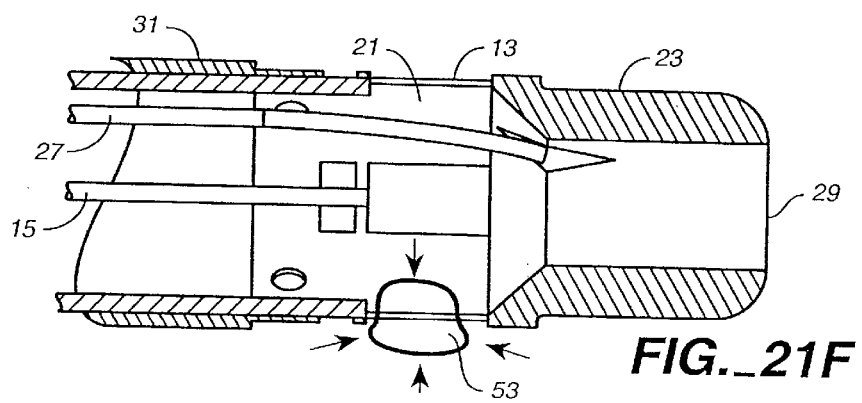
FIG._21F
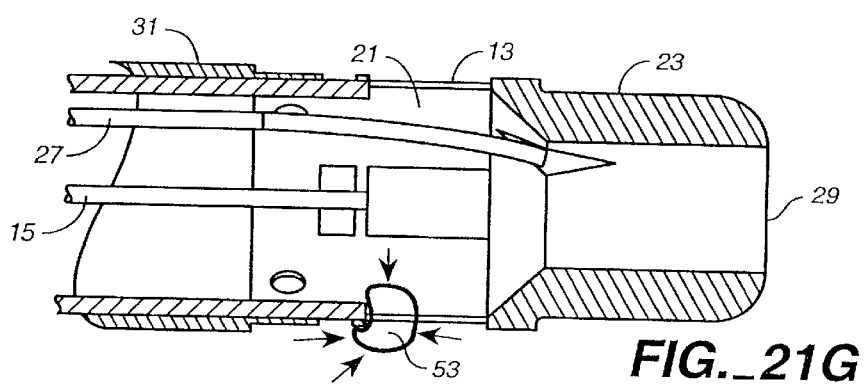
FIG._21G
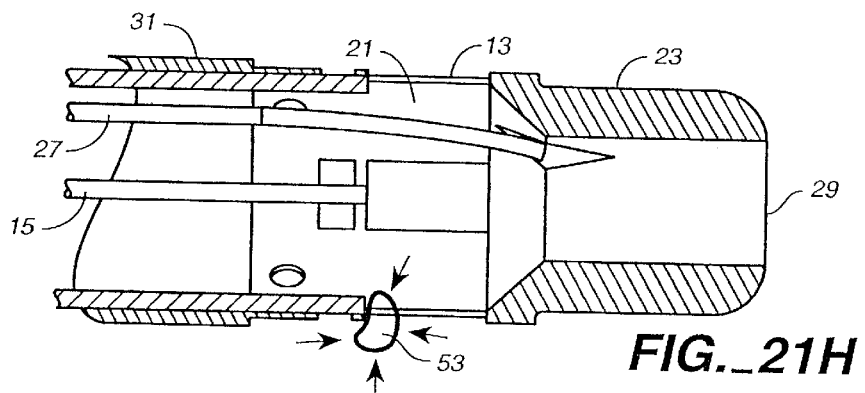
FIG._21H

FLEXIBLE FLOW APPARATUS AND METHOD FOR THE DISRUPTION OF OCCLUSIONS

CROSS-REFERENCE TO RELATED APPLICATIONS

This patent application is a continuation-in-part ("CIP") of U.S. patent application Ser. No. 09/328,514, entitled "Flexible Flow Apparatus and Method for the Disruption of Occlusions," filed Jun. 9, 1999 (herein, sometimes referred to as the "Parent Application"), which is a CIP of U.S. patent application Ser. No. 09/165,435, filed Oct. 2, 1998, now U.S. Pat. No. 6,210,400 B1, which is a CIP of U.S. patent application Ser. No. 09/120,598, filed on Jul. 22, 1998, now U.S. Pat. No. 6,139,543, the entireties of all of which are therein incorporated by reference. This patent application is related to U.S. patent application Ser. No. 08/955,858, entitled "PhotoAcoustic Removal of Occlusions From Blood Vessels," filed on Oct. 21, 1997, and to U.S. patent application Ser. No. 09/113,700, entitled "Apparatus for Delivering Radiation Energy," filed on Jul. 10, 1998, the entireties of both of which are herein incorporated by reference.

BACKGROUND OF THE INVENTION

The above-referenced U.S. patent application Ser. Nos. 09/120,598, 09/165,435, and 09/328,514 (the "Preceding Applications"), form the background of the present invention. In these Preceding Applications, the inventors disclosed their inventions as generally relating to at least partial removal of occlusive material from a body lumen or vessel with acoustic phenomena resulting from radiation energy pulses delivered through optical fiber media to the vessel. The inventors disclosed their inventions as relating more particularly to methods and apparatus for generating fluid flow within a body vessel to facilitate disruption of occlusive material and recanalization of the occluded vessel. The inventors used the term "clot" to refer to a thrombus, embolus or some other partial or total occlusion of a vessel, and the term "emulsify", or the term "chew", to mean to disrupt occlusive material by photoacoustic or mechanical or other phenomena to generate particle(s) smaller than the original occlusive material. These terms also apply to the present invention.

In the Preceding Applications, the inventors disclosed techniques and apparatus that use pulsed radiation energy to generate fluid flow and/or to perform mechanical work within a body lumen or vessel. These techniques and apparatus were disclosed as being useful to recanalize a body vessel by disrupting a partial or total occlusion therein. These techniques and apparatus were disclosed as having application in the removal of such an occlusion or obstruction from a vessel within the human body, and more particularly, a partial or total clot from a cerebral blood vessel, where that clot has caused ischemia or an ischemic stroke. These techniques and apparatus were disclosed as being particularly useful for timely removal of such a clot to avoid causing collateral damage to the vessel.

The above-referenced Preceding Applications, the inventors disclosed methods and apparatus for attracting occlusive material within a vessel to a photoacoustic source of disruption, so as to potentially enhance the amount and/or degree of disruption obtained. The apparatus was disclosed as being flexible at its distal tip to facilitate access to occlusive material that may be located in a remote, tortuous vessel pathway.

The foregoing and other principles of the Preceding Applications have application in the present invention.

SUMMARY OF THE INVENTION

The present invention generally provides an apparatus having at least one inlet port, at least one outlet port, and at least one optical fiber having a distal end positioned relative to the ports such that when pulsed radiation energy is delivered to a body vessel via the optical fiber, fluid is caused to pass through the inlet port and to travel towards the outlet port, preferably past the optical fiber distal end. The repetitive formation and collapse of bubbles in the ambient fluid creates this flow phenomenon, which in turn results from the repetitive absorption of radiation pulses by the fluid. This flow phenomenon can be used to enhance the total or partial mechanical disruption or emulsification of occlusions with photoacoustic phenomena (as described in the above-mentioned Ser. No. 08/955,858 application) by causing ambient fluid and occlusive material to be drawn towards the recanalization apparatus. The invention can also result in localized emulsification of occlusive material or partial or complete removal of that material from the body. The capability of radiation energy to cause mechanical work to be performed is demonstrated by the present invention.

Multiple fibers can be arranged in such a manner that one or more fibers generate the pumping phenomenon and/or one or more fibers contribute to the clot emulsification by generating the acoustic phenomena described in the Ser. No. 08/955,858 application, and/or one or more fibers contribute to mechanical disruption of the clot as disclosed herein, for example. Multiple outlet ports are arranged in various tubing materials in such a way as to maintain a flexible distal tip portion of the apparatus while also maintaining column strength of the distal portion.

The use of very small diameter optical fibers allows the desired pumping to be achieved and acoustic waves to be generated with a relatively low amount of radiation pulse energy, thereby keeping the amount of heat input to the vessel at a low level. Proper thermal management according to the present invention reduces the likelihood of damaging the walls of the blood vessel adjacent the occlusion, which is especially important for the relatively thin walled vessels of the brain in which the invention has application. Accordingly, radiation pulses not causing the desired fluid flow or not being efficiently converted into the desired acoustic waves may be terminated in order to prevent providing energy that heats the region without doing useful work, as has been described in the above-mentioned related applications.

The present invention encompasses methods and flexible apparatus for delivering radiation energy to a radiation-absorbing fluid within the apparatus to generate a series of expanding and collapsing bubbles therein, and thereby generate flow in a fluid surrounding the apparatus. Effective fluid flow is obtained via at least one optical fiber, disposed within the apparatus near a distal opening therein, that, when fired, tends to pump fluid with respect to the apparatus, and at least one other optical fiber, disposed within the apparatus in the vicinity of a side opening thereof, that, when fired, tends to agitate fluid near its distal end.

Preferably, the apparatus includes one "pump" fiber and multiple "chew" or emulsification fibers, such as four chew fibers. The pump fiber is preferably secured within a distal section of the apparatus at a point proximal to the distal opening. The chew fibers are preferably arranged within an intermediate section of the apparatus, proximal to the distal section. Preferably, this intermediate section has a number of openings that corresponds to the number of chew fibers. In this embodiment, each of the chew fibers is arranged such that its distal end is located in a vicinity of a corresponding opening and can act upon fluid located near or passing through that opening.

The pumping and chewing actions of the fibers within the device cause a net fluid motion that is particularly effective in disrupting a partial or total occlusion in a body passage, such as a blood vessel, within which the apparatus is operated. While a relatively low level of radiation energy or power may be used for such applications, such as the energy or power level disclosed in the Preceding Applications, it may be desirable to increase the energy or the power to obtain greater disruption effects. The present apparatus is adapted to provide a cooling medium to the body passage to avoid causing any substantial thermal injury to the walls of the passage, particularly when the apparatus is operated over a broader range of power parameters. By way of example, the apparatus may be operated using an applied power level of from about 0.5 to about 2 W to obtain an average power level at the distal end of the apparatus of from about 0.5 to about 2 W, or of from about 0.5 to about 1.5 W using a duty cycle, as may be desirable or necessary. The apparatus may be operated at the higher levels within these ranges particularly when active cooling is provided.

Active cooling encompasses the provision of a cooling medium through a lumen of the apparatus to its intermediate and/or distal sections, from which the medium may travel within the apparatus and/or out of the openings therein into the body vessel. The cooling medium is a radiation-absorbing fluid, such as blood or a dye-based coolant, such as a coolant containing blue dye. A suitable coolant may be chosen based on a variety of factors, such as the selected radiation and the radiation-absorption characteristics of the coolant for that radiation, or the viscosity characteristics of the coolant, for example, a viscosity conducive to appropriate fluid mechanics upon operation of the apparatus. The flow rate of the coolant may be varied according to various operational parameters, but will generally be from about 0.5 to about 3 cc/minute.

The present invention allows one to operate the apparatus over broader ranges of energy and power than formerly believed safe or practicable. These ranges include energy and power levels that are more effective in emulsification processes. By way of example, in the disruption of porcine clot, ex vivo, better results have been achieved when using a blood analog coolant and operating the inventive apparatus at an average power of about 1 W, than when using a previous apparatus with the same coolant at the same average power. Further by way of example, in the disruption of porcine clot, ex vivo, even better results have been achieved when using either a red-dye coolant or a blue-dye coolant in place of the blood-analog coolant and operating the inventive apparatus at an average power of about 1 W.

Additional objects, features and advantages of the various aspects of the present invention will be better understood from the following description of its preferred embodiments, which description should be taken in conjunction with the accompanying drawings.

BRIEF DESCRIPTION OF THE DRAWINGS

The drawings include FIGS. 1–21, not all of which are drawn to scale or to the same scale. Like reference letters and numerals are sometimes used in the drawings and in the following description to refer to like features shown or described elsewhere herein. The reference letters and numerals used herein are meant to be internally consistent, such that whether or not they happen to coincide with those used in applications that have been incorporated herein by reference, their meaning will be apparent to those of ordinary skill in the art. It should also be noted that a numbered figure having multiple sub-parts is sometimes collectively referred to by the numbered figure (for example, FIGS. 7A–E may be collectively referred to as FIG. 7). These conventions are adopted merely by way of convenience, and not by way of limitation.

The drawings are now briefly described.

FIG. 1 is a longitudinal cross-section of a device demonstrating the ability to pump fluid, as disclosed in the Parent Application.

FIG. 2 includes front and side partial cut-away views of an apparatus for circulating fluid through the distal end of a catheter, as disclosed in the Parent Application.

FIG. 3 is a longitudinal cross-sectional view of an apparatus similar to that shown in FIG. 2.

FIG. 4 shows end and partial cut-away views of an apparatus for pumping fluid having multiple corresponding side slots and optical fibers, as disclosed in the Parent Application.

FIG. 5 shows the device of FIG. 2 and another device disrupting an occlusion blocking a blood vessel, in cross-sectional view.

FIG. 6 depicts a cross-section of an embodiment for circulating fluid past a bundle of optical fibers, as disclosed in the Parent Application.

FIG. 7A depicts a typical construction, in longitudinal cross-section, for a delivery catheter, as disclosed in the Parent Application. FIG. 7B shows an end-view of a flush fiber arrangement of an embodiment of the invention disclosed in the Ser. No. 08/955,858 application, as disclosed in the Parent Application. FIG. 7C depicts an end-view of a distal fiber arrangement, as disclosed in the Parent Application. FIGS. 7D and 7E detail in longitudinal and radial cross-sections the distal portion of a catheter having a fiber arrangement, as disclosed in the Parent Application.

FIGS. 8A and 8B illustrate in longitudinal and radial cross sections another embodiment of the distal portion of a catheter having a fiber arrangement similar to that shown in FIGS. 7D and 7E, as disclosed in the Parent Application.

FIGS. 9A and 9B illustrate in longitudinal and radial cross sections, respectively, another embodiment of the distal portion of a catheter, as disclosed in the Parent Application. FIG. 9C depicts a simplified overview of an alternate embodiment incorporating multiple outlet ports, each port having multiple holes, as disclosed in the Parent Application.

FIGS. 10A and 10B illustrate, respectively, longitudinal partial- and radial cross-sectional views of another embodiment having multiple side-ports and a beveled tip, as disclosed in the Parent Application.

FIG. 11 depicts a marker band for use with the embodiment shown in FIGS. 10A and 10B, as disclosed in the Parent Application.

FIG. 12A is a side view of a device, in partial cut-away, as disclosed in the Parent Application. FIGS. 12B and 12C are enlarged side and perspective views, respectively, of the distal end of the device of FIG. 12A. FIG. 12D is a side view of a section the device similar to that of FIG. 12A, as disclosed in the Parent Application. FIG. 12E is a schematic illustration of an "over the wire" use of the device shown in FIGS. 12A–D, as disclosed in the Parent Application.

FIGS. 13 and 14 are schematic illustrations of the operation of a device such as that of FIG. 12A or 12D, as disclosed in the Parent Application. FIGS. 13A–F and 14A–D schematically illustrate such operation over time.

FIG. 15A is a side view of a distal end of a device, in longitudinal cross-section, according to an embodiment of the present invention. FIG. 15B is a perspective view of the distal end of the device of FIG. 15A. FIG. 15C is a perspective of a distal end of a device that is a variation of that of FIG. 15A, according to an another embodiment of the present invention. FIG. 15D is a horizontal cross-sectional view of the distal end of the device of FIG. 15A, along lines D—D of that figure.

FIG. 16A is a longitudinal side view of a distal end of a device, according to an embodiment of the present invention. FIG. 16B is a perspective view of the distal end of the device of FIG. 16A. FIG. 16C is a horizontal cross-sectional view of the distal end of the device of FIG. 16A, along lines C—C of that figure.

FIG. 17 is a perspective view of a distal end of a device, according to an embodiment of the present invention.

FIGS. 18A and 18B are perspective views of a portion of a distal end of a device, according to an embodiment of the present invention, is partial disassembly and assembly, respectively.

FIG. 19 is a bar graph showing a rate of chewing performed by various devices described herein, when operated at different power levels.

FIGS. 20 and 21 are schematic illustrations of the operation of a device such as that of any of FIGS. 15–18, according to the present invention. FIGS. 20A–H and 21A–H schematically illustrate such operation over time.

DESCRIPTION OF THE PREFERRED EMBODIMENTS

The present invention may, in general, be applied to the disruption of material forming a partial or total occlusion of any human vessel but is particularly directed to opening a blood vessel that is totally or substantially blocked to the flow of blood. The related patent applications that have been incorporated by reference (above) disclose these general applications of the present invention, as well as the associated configurations and operating parameters of the associated technology, including, for example, the methods and apparatus for delivering radiation energy from the laser to the optical fibers. Those disclosures apply equally to the present invention. However, it should be understood that the present invention is not limited solely to addressing the disruption of occlusions from blood vessels but may have additional applications in which generating fluid flow within a vessel is required or desired, as will be understood upon reading this disclosure.

The present invention encompasses devices, including catheters, having the ability to emulsify or chew through an occlusion by generating flow through an active distal portion to help draw the occlusion towards the optical fibers (and thus towards the source of the acoustic pressure and shock waves and other forces). These catheters promise to be able to create a hole in an occlusion relatively larger than the outside diameter ("OD") of the catheter or device being used.

Illustrating the types of flow generated by the present invention is the apparatus shown in FIG. 1 comprising an optical fiber positioned inside a capillary tube. Mounting a fiber inside a capillary and firing short duration, low energy, high frequency pulses of absorbable radiation energy creates several useful phenomena. First, generating a series of bubbles 320 inside the sheath portion 322 of the capillary 324 through short-duration, high-frequency, low energy radiation pulses delivered via optical fiber 326 to a fluid medium 328 capable of absorbing said radiation results in a rather violent fluid jetting from the distal end of the capillary in the direction shown by arrows 330. This is believed to result from the expansion of the bubble out of the capillary and into the surrounding media, forcing outwards the slug of fluid that originally occupied the portion of the capillary between the fiber tip and the distal end.

Second, a rather vigorous pumping action was observed during the delivery of pulses of radiation to the fluid, in which fluid shot out of the top of the capillary as indicated by arrows 332. It is believed that this pumping action resulted from the repetitive collapse of bubbles. It is believed that bubble collapse created a zone of low-pressure inside and adjacent to the distal portion of the capillary, which in turn caused surrounding fluid from the vessel to rush back into the capillary to fill the void left by the collapsing bubble. It would appear easier for fluid in the vessel to fill the void rather than fluid already present between the capillary wall and the fiber, because the former would experience less resistance to flow. It is believed that this rapid fluid refilling of the void facilitated the observed flow out of the proximal end of capillary. Capillary action may also have played a role in this first embodiment, although capillary action is not necessary to generate fluid movement, as further explained below.

These pumping/sucking phenomena can be utilized in a variety of apparatus within the scope of the present invention. One such apparatus is shown in FIG. 2. Outer sheath 334 surrounds one or more optical fibers 338 (three are shown for illustration) asymmetrically arranged in the sheath. The distal tips of the fibers 338 are positioned relative to sheath side slot 336 in such a way that fluid present in the vessel is sucked through side slot 336 and forced out the distal end of the sheath 340. The dimensions of the side slot relative to the fiber size and position are important, since if the fibers are located incorrectly, the pumping/sucking phenomenon is not observed. Satisfactory results are achieved with 12 fibers, having a 50-micron core diameter, a 55-micron clad diameter and a 65-micron polyimide buffer diameter (sometimes referred to as "50/55/65" fibers), aligned side-by-side, with their distal tips even and extending about ⅓ mm (A) into a ⅔ mm-deep slot (A+B), which was ⅓ mm (C) from the distal tip of the 3 French catheter of 0.022 inch inside diameter ("ID"). Note that FIG. 2 (including lengths A, B and C) is not drawn to scale. The slot was horizontally sized to match the width of the 12-fiber bundle.

More particularly, 25 ns pulses (separated by about 200 microsecond delays) of 532 nm wavelength radiation (selected for its absorption characteristics in blood) at a frequency of about 1 to 10 kHz (with 5 kHz preferred) were introduced through each of the twelve fibers in bursts of 1–3 pulses per fiber with an energy/pulse of about 100 to 300 microJ and an average power of about 300 milliW. A frequency-doubled Nd:YAG laser was used to produce the desired wavelength light. Clot adjacent slot 336 was sucked into the catheter and emulsified via a combination of shock and acoustic waves and turbulence caused by the expansion and collapse of bubbles in the fluid. The emulsified material was then directed out of distal tip 340 and back into the fluid.

It is believed that the edge of slot 336 also contributed to the emulsification by tearing the clot as it entered the turbulent region adjacent the optical fiber tips. This mechanical disruption by the edge also resulted from the bubbles hammering the clot against the edge during emulsification. The sucking motion at slot 336 creates a small vortex which circulates the emulsified material exiting end 340 back towards slot 336 as distance C approaches less than 0.25 mm. This vortex action appears to help keep the clot in contact with the slot once the clot is first sucked in, and thus aids further emulsification.

As with all embodiments of the invention, the laser parameters, such as the pulse duration, the pulse frequency, the wavelength, the pulse energy, and the power, and the like, may be varied while still producing the desired phenomena. By way of example, it is possible to use a pulse duration of between about 5 and about 30 ns, such as 25 ns; a pulse frequency of from about 1 to about 10 kHz, such as about 5 kHz; an energy per pulse of about 100 to about 500 µJ, such as about 300 µJ; a power of about 0.5 to about 2 W, such as about 1.5 W, where a duty cycle of from about 50% to about 90%, or to about 75%, such as 66.7% (for example, 200 pulses "on" and 100 pulses "off"), may be used to arrive at an average power of from about 0.5 to about 1.5 W, such as about 1 W; provided appropriate cooling, such as the active cooling further described herein, is used when necessary to manage the heat within the vessel to minimize or prevent damage to the vessel wall. As mentioned previously, use of a duty cycle may not be required, such that the average power delivered at the tip of the apparatus may be the same as the total available power, namely, from about 0.5 W to about 2 W. Typically, this active cooling will be employed when the power level is at the relatively high end of the range provided above, such as a relatively high average power level of above about 350 mW. Active cooling may include providing a biocompatible coolant within the sheath 334 using a coolant flow rate of from about 0.5 cc/min to about 3 cc/min, such as about 1 cc/min, wherein the coolant has suitable viscosity and radiation-absorption characteristics, as further described herein, particularly in relation to the embodiments of FIGS. 15–18.

FIG. 3 is a sectional view of a side-sucking apparatus similar to that shown in FIG. 2. Distal tip 339 containing slot 336 is shown attached to outer catheter wall 334, typically with glue such as cyanoacrylate. The distal end of optional inner lumen walls 354 can terminate evenly with the tip of optical fiber(s) 338, which makes polishing of the fiber and catheter tips during catheter construction easier. As shown in FIG. 3, the volume of the outlet port 340 can be decreased to form annular space 356 by inserting mandrel 350 through inner lumen 352 formed by inner lumen walls 354. Decreasing this volume increases the velocity with which the emulsified clot is expelled from the outlet port 340. Typical materials of construction for the distal tip 339 include HDPE, LDPE, PET, polyimide, or even a metal. Typical distal dimensions are those of a 3 French catheter, although proportionately larger or smaller devices may be constructed depending upon the size of the vessel to be accessed.

An example of a catheter that may be used to deliver the embodiment shown in FIG. 3 as well as other embodiments of the invention to the occlusion site is shown in FIG. 7A. The delivery catheter may comprise two concentric tubes. The outer and inner tubes may comprise multiple sections of decreasing flexibility. As an illustration, FIG. 7A shows three outer sections and two inner, although other combinations may be used. In a 150 cm catheter, for example, outer sections 380, 382, and 384 may be anywhere from about 50–120 cm, about 25–95 cm, and about 3–20 cm, respectively. Sections measuring 95 cm, 50 cm, and 5 cm, for example, produce satisfactory results. A satisfactory proximal outer section 380 comprises a composite of polyimide/spiral stainless steel tubing, with an inner diameter, for example, of 0.030 to 0.040 inch, such as that made by Phelps-Dodge High-Performance Conductor. Section 380 is glued with, for example, cyanoacrylate glue 392, to mid outer section 382 comprising high-density polyethylene (HDPE). The HDPE facilitates joining the more rigid composite proximal outer sheath to the soft distal outer section 384, to which section 382 is glued. Section 384 comprises plasticized polyvinylchloride (PVC) of 60–65 Shore A hardness. The inner tube comprises glued sections 388 and 390 having lengths of anywhere from about 120–140 cm and about 10–30 cm, respectively. Proximal inner section 388 has a material selected to provide the desired rigidity and high burst pressure, such as polypropylene tubing with flex modulus (psi) of between about 200,000 and about 250,000, with about 220,000 being typical. Distal inner section 390 may comprise a LD polyethylene/EVA blend. A 9% EVA/LD polyethylene blend is satisfactory.

A radiopaque band marker 386, of gold or platinum, may be added to the distal tip of the catheter to facilitate fluoroscopy. The marker band is glued to the distal outer tubing, either outside of the distal outer portion or abutted against the distal edge to be flush with the outer wall. The marker band may take any of a variety of forms, such as any of the forms described in embodiments herein.

In general, the inner tube materials are chosen for their burst properties, lubricious characteristics and the outer for their rigidity or softness. Similar materials having similar relative properties of flexibility, softness, and lubricity, may be substituted for those disclosed for the inner and outer tubes. Fibers 394 lie freely between the inner and outer concentric tubes, anchored in place only by the various glue points shown to facilitate increased flexibility. A more rigid catheter may be achieved by injecting more glue at various points between the two tubes of the constructed apparatus. One or more stainless steel or nitinol mandrels 396 may also be inserted between the inner and outer tubes to create more rigidity. The mandrel may be anchored in place by glue points 392 and 398. A mandrel of 0.004 inch diameter may be used, although other diameters or a tapered mandrel would be acceptable, depending on the desired degree of rigidity/flexibility of the construction.

Although not shown in FIG. 7, the body of the catheter may have other constructions. One variation would include a braided inner shaft having a variable stiffness, increasing in flexibility from the proximal to distal ends. Such a variable stiffness braid is available, e.g., from HV Technologies of Trenton, Ga. Another variation includes the addition of a fourth distal section to the outer wall of the catheter to further improve the flexibility of the distal portion of the device, and to help to prevent possible kinking under certain circumstances at the junction of sections 382 and 384, which typically are of HDPE and PVC, respectively. This fourth section may comprise a soft polymer, such as low-density polyethylene (LDPE), which may be connected to the high-density polyethylene section (HDPE) 382 by gluing or melting, and to the distal outer PVC section by gluing. Melting is preferable, if practical, to lower the outside diameter of the combination of the two materials. Satisfactory constructions that minimize or avoid kinking at the section 382–384 junction have been made by replacing the distal 5 cm of the HDPE section 382 with about the same length of LDPE. For such a construction, the 0.004-inch-diameter mandrel, typically of nitinol, preferably would extend to the junction of the HDPE/LDPE section.

An alternate construction of the distal portion of the body sheath would be to strengthen the transition between the HDPE/PVC or LDPE/IPVC junction on the outer wall, by, e.g., adding shrink-wrap over the joint and 1–2 cm on either side of the joint, or adding shrink-wrap to the entire length of the device, the shrink-wrap terminating 1–2 cm distal of the joint to be supported. Other modifications will be understood, and thus will not be further addressed herein.

Dimensions for the materials for the inner and outer walls of the catheter can be chosen based on availability, desired flexibility, strength and resiliency. By way of example, acceptable dimensions for a 3-French device are about 0.022/0.026 inch inner/outer diameter for the inner lumens and about 0.031/0.035 inch inner/outer diameter for the outer lumen, with a typical marker band having about 0.034/0.037 inch inner/outer diameter and a length of about 1 mm.

A lubricious polymer coating, such as a hydrophilic coating or silicone may be used to increase the ease of navigating the catheter through the guiding catheter and desired body lumens, and if introduced on the interior catheter walls, may enhance the ability to track over an associated guide wire.

In general, catheter construction is well known and thus will not be described in great detail. Within the scope of this inventions are catheters that possess an appropriate balance of flexibility, stiffness, and longitudinal strength, among other factors, to be useful in reaching occlusive material with a vessel, particularly a cerebral blood vessel, and treating the obstructed vessel in the manner previously described. In brief, after inserting the desired number of optical fibers and the inner tubular member into the outer tubular member, the distal location of each fiber is adjusted so that the fiber distal ends occupy the desired distal geometry. For example, the fibers can be sequentially arranged in the same order as in the planar array of the connector (not shown) to the energy source, so that they occupy the geometry shown in FIG. 7B (as an example of a configuration that could be used for the embodiments disclosed in the Ser. No. 08/955,858 patent application) or in FIG. 7C (that would correspond to the embodiment shown in FIGS. 2 and 3). Arranging the fibers in this manner ensures that the energy source, such as a laser, which supplies energy to the fibers via the connector, supplies energy to the desired fiber(s) in the desired order or pattern. To accomplish this fiber arrangement, a light source, such as a marker laser, is used to identify which fiber distal end corresponds to which fiber end positioned in the connector. As each fiber is sequentially identified, its distal end is temporarily held in position until all fibers have been identified and located. The fibers are then glued into position. Fibers can be held temporarily in position by inserting each distal end into an alignment block having a series of holes, each hole corresponding to a particular fiber. The block holds the fibers in position until they are glued.

Fluid such as biocompatible coolant (e.g., saline, blood, or a dye-based coolant), radiographic agent or thrombolytic agent may be introduced through inner lumen 352 during emulsification. Further, fluid may be aspirated through the lumen, for example, to remove emulsified material from the body.

FIG. 4 depicts a catheter in which multiple fibers are mounted approximately equidistant around the circumference of the catheter, each fiber having its own inlet port in the side of the catheter tip. When the fibers are fired individually with pulsed radiation, as described herein, each fiber creates its own pumping action through its corresponding side hole 358. As the position of the distal tip of an optical fiber moves up its side hole towards the distal tip of the catheter, the pumping phenomenon tends to change from sucking through the side hole to blowing out of the side hole. When the tip of the catheter is located in fluid adjacent the occlusion, such an arrangement of fibers can cause the end of the catheter to gyrate around the clot, thereby increasing the degree of emulsification of the clot relative to a catheter that remains relatively stationary. Gyration can be improved by decreasing the number of fiber-and-slot combinations and increasing the number of consecutive pulses to each fiber, to permit the catheter tip to overcome inertia and to move through the fluid across the face of the clot. Gyration, however, is minimized if the catheter tip is located within an occlusion, due to high damping forces.

The bottom of FIG. 5 shows how the device depicted in FIGS. 2 and 3 may be used in a blood vessel 360 having a thrombus 362 and stenotic plaque 364. For the device shown in FIG. 2, the catheter can be punched through the thrombus while the optical fibers are dormant until the catheter reaches the distal position shown. Pulsed radiation is then delivered down one or more optical fibers 338, causing the thrombus to be sucked into slot 336, emulsified, and then ejected 366 through the catheter distal tip. During the procedure, the catheter tip is slowly withdrawn through thrombus 362, thereby revealing new thrombus to the catheter tip for emulsification. The speed of withdrawal is dependent upon the character of the thrombus being emulsified and the geometry of the fibers and slot. The catheter should not be withdrawn so fast that the catheter'ability to chew through the thrombus is overwhelmed and the catheter tip becomes clogged, thereby adversely affecting the degree of emulsification. While FIG. 5 depicts thrusting the catheter tip of FIG. 2 entirely through the thrombus before emulsification begins, it may also be used to emulsify thrombus by simply causing the catheter tip to approach the proximal portion of the thrombus with the optical fibers already firing into the ambient fluid so as to create the desired acoustic phenomena and avoid direct ablation, as schematically illustrated by device 401 at the top of FIG. 5, which may be any of the devices described herein.

The apparatus shown in FIG. 6 can establish either forward or reverse flow depending on the position of the tip of the fiber optic bundle 400 relative to the distal opening 426. When the fiber optic bundle 400 is positioned within about 0.004 to 0.006 inch from the distal opening 426 of the HDPE 1-mm diameter sheath 424, suction is developed through opening 426 and fluid is expelled through rear opening 428. Alternatively, if the distance between the distal tip of the fiber optic bundle 400 and the distal opening 426 is either increased or decreased outside of the 0.004 to 0.006 inch range, the flow mechanism reverses, and the device develops suction through opening 428 and expels fluid through distal opening 426. The same would be true for differently sized devices, as long as the bubble size produced by the fiber/energy/operating conditions combination were sufficiently large.

Traditionally, pumping or suction of fluid within the body has been achieved by having an external source of suction or pressure generate a corresponding negative or positive pressure inside the body cavity. The fluid jetting/suction phenomenon of the present invention, however, illustrates how fluid can be pumped inside the body cavity (or in any other remote source of fluid) using radiation energy from a radiation source remote from the point of fluid flow. Pumping fluid using the methods described is believed to result in relatively high, albeit fleeting, pumping pressures of perhaps several hundreds of psig, for example, from about 100 to about 200 psig. Such pressures were previously unattainable in the body without risk of injury.

In the various embodiments, an inner lumen, such as inner lumen 352 of FIG. 2 or FIG. 3, may be used to deliver fluids such as radiographic contrast agent or coolant to the site of the occlusion. Since all embodiments of the invention rely on the absorption of select wavelength radiation energy into colored fluid such as blood, however, delivering fluid to the area of emulsification that alters the color of the vessel fluid through dilution or dissipation, may interfere with the absorption characteristics of the environment of the occlusion. Small delays in the emulsification process thus may be necessary to permit the area surrounding the environment to reperfuse with fluid, such as blood, that is capable of absorbing the wavelength light being used, if fluid is introduced to the site of the occlusion through the central lumen. Alternatively, a tinted fluid compatible with the ambient conditions of the occlusion, may be introduced, so that absorption of the radiation energy will be minimally affected by the introduction of other fluid.

FIGS. 7D and 7E are schematics of the distal end of the catheter shown in FIG. 7A (previously described) having a configuration with an active tip portion similar to that shown in FIG. 12A, but having a single "pumping" fiber 391 and three "chewing" fibers 394. Tube 389, having a length of approximately 1 mm and an inner diameter of from about 0.014–0.018 inch, is glued between the distal inner walls 390 of inner diameter of from about 0.020 to 0.029 inch. Tube 389 has a 0.35 to 0.5 mm-deep notch 393 cut out of one side. The major distal portion of "pumping" fiber 391 is located between inner catheter wall 390 and outer catheter wall 384. The minor distal portion of fiber 391 passes between the joint of inner walls 387 and 390 and is secured to the outer surface of tube 389 such that its distal tip is located about 0.25 mm from the distal-most edge of tube 389, which is substantially coplanar with the distal-most catheter plane 391a. Tubular portion 387 (e.g., of low-density polyethylene) is glued on the distal ends of wall 390, so that its distal edge is flush with the distal edge of tube 389. Marker band 386 is added to facilitate visualization of the apparatus inside the body during use. The overall distal diameter of the construction is about 1 mm or 3 French.

Side slot 397 is formed by skiving both the inner and outer walls of the catheter, and serves to eject from the apparatus fluid and emulsified material pumped in through tube 389 as a result of the action of fiber 391. The slot, typically of 3 to 10 mm long, may begin anywhere from 1 to 10 mm from the distal tip of the catheter. As the distance between the distal tip of the catheter (and thus of the fiber 391) and the slot increases, however, less pump head exists to eject pumped fluid and emulsified material. More than one slot may be used, as desired. Minimizing the spacing between fiber 391, tube 389 and tube 387 can improve the pumping performance of fiber 391.

Fibers 394 can be positioned approximately flush with the distal tip of the catheter construction, and thus may not contribute to the pumping action. Instead of being secured with a glue plug as shown in FIG. 7A, however, fibers 394 are anchored to the side wall of either portion 387 or 390 using a small patch of glue 395. Thus, if fibers 394 are positioned such that they both emulsify and create a sucking force, particulates sucked into the apparatus by fibers 394 can travel between the inner and outer walls and be ejected through side slot 397. Alternatively, the emulsified particulates might potentially be trapped between the walls and withdrawn from the patient after recanalization.

Although only one pumping fiber and three chewing fibers are disclosed in this embodiment, other combinations of fibers are possible, including multiple pumping fibers. Radiation pulses are distributed between the various fibers as desired. Two examples would be to evenly distribute groups of three pulses of energy with a 0.33 duty cycle between the four fibers, so that each fiber receives 25% of the average energy delivered to the site of the occlusion. Alternatively, the average energy can be delivered evenly between the chewing and pumping fibers, so that each set of fibers receives about 50% of the energy delivered. In the fiber arrangement disclosed in FIGS. 7D and 7E, for example, a pulse train could be delivered to the single pumping fiber after every delivery to one of the three chewing fibers, so that for every pulse train received by a particular chewing fiber, the pumping fiber would receive three. Distributing radiation pulses in this manner will help to increase the continuity of the pumping and emulsification actions, and will reduce periods of inaction of the two. In addition, since the pumping fiber alone will tend to attract fluid/particles to the device, and the chewing fibers alone will tend to repel fluid/particles from the device, the pumping and chewing fibers can be controlled to address potential clogging. In other words, if the device starts to become overwhelmed with occlusive material, the pumping fiber could be turned off while leaving the chewing fibers on, so that the material would be emulsified and/or repelled to clear the unit for further pumping/disruption.

Alternatively, the device could be used to probe the vessel for the location of the clot with only the chewing fibers operating, and then based on the duration information provided by the bubble feedback system (bubble duration being less for clot than for blood), the pumping fiber could be turned on once the device reached the vicinity of the clot. In other words, as described in the related patent applications which have been incorporated by reference (above), the pumper and/or the chewer fibers could be controlled using bubble feedback information to avoid inefficiently introducing heat into the system.

FIGS. 8A and 8B depict an alternative construction to that shown in FIGS. 7D and 7E for a similar fiber arrangement. Nozzle 371 may be a solid piece of polyether block amide (such as PEBAX 7233, made by AtoChem) with Shore D hardness of about 70, or some other similar, suitable polymeric material. Nozzle 371 is extruded as a tube with inner diameter equal to the widest portion of the final nozzle construction, and with multiple lumens 369 created within the walls of the PEBAX construction. Because of this construction, the PEBAX cannot be too soft, otherwise the lumens cannot hold their form and collapse. These lumens ultimately will house optical fibers 391 and 394. The nozzle is created by gently heating the PEBAX material and collapsing it around a mandrel with an outside diameter equal to the desired inner diameter of the distal portion of the nozzle. Typically, a nozzle fitting a 3 French, 1-mm-OD catheter has a proximal inner diameter of 0.022 inch, a distal inner diameter of 0.018 inch, a length of about 2 mm, and a 1-mm-long necked portion. Nozzle 371 is secured to the inner wall of the catheter with cyanoacrylate glue. "Pumper" fiber 391, present between inner and outer catheter walls, as previously described, is positioned in one of the lumens 369 of nozzle 371 and terminates about 250 microns from the distal plane of the apparatus, such that it creates a pumping motion, as described herein, that results from pulsed radiation energy. The removed portion 375 of nozzle 371 permits the fiber tip 373 of "pumping" fiber 391 to extend slightly into the inlet port 379. Each of "chewing" fibers 394 is positioned in the pattern shown, for example, inside another lumen 369 in nozzle 371 flush with the distal plane of the apparatus. These fibers act to emulsify occlusive material before such is drawn in through distal port 379 and ejected through side slot 397.

Although side slot 397, as shown, consists of two skives, one in each of the inner and outer wall of the catheter about I cm back from the distal plane of the apparatus, the side slot may also comprise a series of smaller holes in either or both of the inner and outer walls. Replacing a skive in the inner wall, for example, with three smaller holes increases the strength of the apparatus and may prevent collapse of that portion of the device as it is pushed through a body lumen towards the site of an occlusion. In addition, a fiber (not shown) can be positioned in the vicinity of the skives or smaller exit port holes, so that acoustic phenomena generated by that fiber can help to force material out of the exit port(s) and to prevent clogging in the exit port region.

An alternate set of chewing fibers is also shown in FIGS. 8A and 8B. These fibers 377 could be used instead of, or in addition to, fibers 394. The last 1 mm or so of the distal tips of fibers 377 are free. It is believed that free tips contribute to better emulsification, such that fibers 377 may be able to emulsify occlusive material more effectively than fibers 394. Fibers 377 could be positioned by feeding the fiber from in between the inner and outer catheter walls into a lumen 369 of nozzle 371, and then out of a slit in the outer wall of nozzle 371 (at which point it is glued) so that the distal fiber tip is approximately flush with the distal plane of the apparatus.

Marker band 386 is shown in FIGS. 8A and 8B as mounted on the nozzle rather than on the outermost tubular material, another possible location. The inner location as shown provides the advantage of streamlining the distal outer diameter of the apparatus.

It may be desired to have more than one outlet port in the sidewall of the distal tip, especially if the central lumen of the catheter is to be used for aspiration, as described above. Aspiration causes vessel fluid to pass through one or both of the inlet and outlet ports into the catheter, through the central lumen and out of the patient'body, if desired. Having only one outlet port risks possibly having the outlet port suck against the vessel wall, thereby blocking the flow through that port. Blocked flow risks potentially shutting off the pumping action of the pumping fiber, having the tip heat up due to the lack of re-flow through the distal portion of the catheter tip, and possibly having the partial vacuum damage the vessel wall. Having multiple, circumferentially-spaced, outlet ports helps to equilibrate the forces generated by aspiration, and also helps to guarantee that even if one outlet port is blocked by the vessel wall, other outlet port(s) are available to eject material and/or to facilitate aspiration, thereby preventing the vessel wall from being damaged through the partial vacuum. If more than one skive-type outlet port is cut into the catheter tip, however, the column strength of that portion of the catheter may be compromised, such that the catheter cannot be as effectively navigated through tortuous vessel pathways. Column strength in a multiple outlet-port embodiment may be improved by having the multiple outlet ports comprise a series of small holes, as shown, for example, in FIG. 9C. Hole diameters are chosen to be as large as possible (to facilitate flow) without allowing a guide wire tip to pass through during manipulation during a procedure, and while maintaining the desired column strength of the distal portion of the catheter. Holes of 0.011 inch diameter, spaced about 1 mm apart, have produced satisfactory results. Holes can be punctured through the inner and outer walls using a coring tool made from a sharpened hypo-tube.

It is easier to create the outlet port holes—or skives, if desired—and to ensure that they align, by first melting the inner and outer walls together while positioned around a rod of desired diameter and wrapped with a discemable tube of shrink-wrap. The bonded walls are then punctured/cut with the rod still in place to form the outlet ports. Two or more sets of outlet holes may be cut, with three sets currently preferred. If three sets of outlet holes are used, they may be positioned opposite from (542) and roughly 90 degrees on either side (540) of the bundle of optical fibers 544, as shown in FIG. 9C. This bundle of fibers (comprising the pumping and chewing fibers), as shown, runs down one side of the length of the catheter to the distal section, at which point the bundle divides into the individual fiber tips that form the desired distal-most array shown, for example, in FIG. 9B. Although the sets of holes shown in FIG. 9C each are similarly and evenly positioned with respect to one another, the holes—either individually or in sets—can be longitudinally and/or radially staggered from one another, which can further improve the integrity of the sheath.

When the inner and outer walls are melted together, it is desirable that the melted portion have roughly the same outer diameter as the unmelted portions, to present a uniformly smooth outer surface to the vessel wall. Some wall materials, however, such as soft PVC and LDPE/EVA blend, if not reinforced in some way, may melt to provide a slight depression in which the outlet port(s) would have to be cut. To prevent this partial surface collapse, a length of reinforcing material, such as a soft PEBAX, capable of bonding to the inner and outer tubings when melted and long enough, for example, to span the entire outlet port, may be inserted between the inner and outer walls. This reinforcing material helps the melted inner and outer materials to retain their original dimensions, facilitates bonding between the two tubings, and also strengthens/prevents from tearing the multiple outlet holes.

Flexibility of the various distal tip constructions of the present invention can be improved in a number of different ways. First, the amount of glue used in constructing the apparatus should be limited. The more glue that is used, the stiffer is the final construction.

Second, softer, more flexible materials may be used for the distal portions of the inner and outer tubular portions of the catheter construction. For example, soft PVC has been successfully used for both inner and outer distal walls. Wall materials, such as PVC, desirably are soft enough to render the distal portion sufficiently flexible to navigate the desired tortuous path, but also stiff enough to permit successful navigation without buckling. If PVC is used, colorless PVC is preferred, so that positioning of the fibers can be visualized through the walls, although colored/opaque PVC could also be used. Positioning the outer PVC tubing over the inner PVC tubing is accomplished by using isopropyl alcohol as a lubricant, which later evaporates during the melting process.

Third, distal tip flexibility can be increased by moving the outlet port(s) further proximal from the distal-most portion of the apparatus. The melting of the inner and outer tubular portions 384 and 390, done as part of the creation of the outlet ports, can tend to melt the optical fibers into the tubular walls, creating a stiffer section of the catheter in which the ports are cut. While being slightly less flexible, this stiffer section aids in preventing immediate kinking at the site of a skived outlet port. Moving this melted portion further away from the distal-most portion of the apparatus permits a longer and more flexible section distal of the outlet port. Having the distal-most portion of the outlet port, or series of outlet holes positioned 3 cm or more from the distal-most end of the apparatus has improved flexibility over distal tips having the outlet port positioned about 1 cm from the distal-most portion.

Positioning the outlet ports further back from the distal-most portion, about 3 or more cm away, has been discovered to have the added advantage of creating more of a cooling effect at the distal tip of the apparatus than was previously observed. It is believed that this added cooling effect is due to there being more fluid circulating between the inlet and outlet ports—due to their being positioned further apart—which helps to absorb more of the heat generated by the pumping and chewing fibers as they create the desirable photoacoustic phenomena to produce flow and/or disrupt occlusive material. These more proximal outlet ports, if skived, preferably have a minimum major dimension of about 4 mm.

FIG. 9A illustrates an alternative method of mounting the pumping fiber 514. In FIG. 9A, tube 520 may comprise, for example, polyimide tubing with a nominal major length of about 1 mm, with portion 522 removed leaving a minor length of about 0.5 mm. Fiber 514 passes from the substantially annular space between inner tubular wall 390 and outer tubular wall 384, through a hole or slit 532 in the inner wall 390 qf the catheter distal tip, and into the inner lumen. The distal tip of pumping fiber 514 is then secured to tube 520 with glue, such that its tip extends about 250 microns past the lowest point of tube 520 and is located about 250 microns from the distal plane of the catheter, for the catheter dimensions described herein, such that delivery of short duration, high frequency, low energy pulses of radiation create the pumping and acoustic phenomena described herein. Tube 520 is glued to the inside of the inner walls 390 of the distal tip of a catheter. Fibers 516 (five shown, as another example) are positioned between inner catheter wall 390 and outer wall 384. The apparatus tip can also be convex, as shown, to aid in navigating body vessels and to eliminate any potentially sharp edges.

In connection with the desire to avoid unnecessary heating at the distal tip of the catheter, described briefly herein and in the patent applications incorporated by reference, any of the preceding embodiments may include a thermocouple or other suitable temperature-sensing device, if desired, to monitor the temperature of the site of the occlusion during operation of the invention. Said thermocouple should be positioned to provide accurate temperature information about the distal tip of the apparatus. Positioning the thermocouple, for example, in the substantially annular space between the inner and outer catheter walls is satisfactory. The thermocouple tip preferably is longitudinally located between the distal tips of the pumping and chewing fibers, although it may also be, for example, substantially flush with the distal-most portion of the apparatus, and is preferably encapsulated (e.g., in glue), to isolate the thermocouple from ambient fluids for biocompatibility reasons. Avoiding flush placement of the thermocouple avoids the potential for damaging the thermocouple tip during final polishing of the distal tip of the apparatus. Shown in FIG. 9B is the preferred thermocouple tip 538 radial position, roughly midway between adjacent chewing fibers 516 on the inner tubular wall (close to the center of the device) and offset from the pumping fiber 514 by about 90 degrees. This positioning produces satisfactorily representative temperature readings for the apparatus without being skewed by the energy output of any one particular fiber. Other locations for the thermocouple tip are also possible. The temperature information produced by the thermocouple could be used to trigger an audio or a visual alarm or to control the laser to avoid further heating of the operation site once the temperature of the distal tip exceeds, for example, 50 degrees Centigrade.

FIG. 10 depicts another embodiment of the present invention, which is a variation on the "windowed" device depicted in FIG. 4. The distal end of the device shown in FIG. 10 comprises a number of side windows 682. Three windows are shown, although two or four (as shown in FIG. 24) or more, up to 12, may also be used. Windows 682 are preferably roughly evenly distributed around the surface of marker band 690, although other distributions are possible. In FIG. 10, for example, the three windows are offset by 120 degrees or so from one another, although 90-degree offsets have also been used with satisfactory results. Each window has a dedicated optical fiber 684 mounted therein, to create flow entering through distal port 686 and exhausting through the windows 682. Inner shaft 688 terminates about midway up each window, with each optical fiber, secured to the inner shaft 688 in the usual manner, positioned such that its tip is roughly midway between the terminus of the inner shaft and the distal-most portion of the window. For a 3-French device, typical dimensions for the windows in a 3-window device with a 1-mm-deep marker band are a width of about 200 microns and a length of about 500 microns, with the fiber tip mounted about 125 microns from the distal-most side of the window, and about 250 microns from the distal-most edge of the marker band (and thus of the device).

As shown in FIG. 10, windows 682 preferably have angular (e.g., square) corners and ends. It is believed that windows with angular corners may better disrupt occlusive material, as material is pulled in through port 686 and expelled through the windows, as compared to windows having circular ends or rounded corners. Square comers can be created by cutting the marker band with a razor blade while the marker band is mounted on a mandrel. Rounded-end windows can be created by drilling two holes into the marker band material and then cutting out the intervening material with a razor blade. Alternatively, the features may be fabricated using standard laser machining or micromachining techniques.

Returning to FIG. 10, marker band 690 preferably has a beveled distal-most section 692, to minimize or prevent inadvertent damage to the interior surfaces of the vessel walls through which the device must pass to reach and/or treat the occlusive material. Additionally, the bevel can constrain the path of a guide wire so as to prevent direct exposure with laser light from the optical fiber 684. Beveled section may be created by rolling the marker band on a hard surface while the band is mounted on a mandrel so that the proximal portion of the marker band is protected from beveling. Alternatively, a simple beveling or chamfer tool may be used to reproducibly apply the desired bevel to a marker band. For a 1-mm deep marker band, typical bevel dimensions are about 0.0025 inch deep and about 40 degrees from vertical (angle α) (measured using a protractor during beveling). A thicker marker band material may be used, for example, 0.003-inch wall thickness, so that a similar beveled surface may be constructed by chamfering the edges of the marker band.

Various methods of attaching the marker band to the body of the device can be used, including simple abutment, abutment with one or more holes (preferably, four holes of 0.005-inch diameter) in the proximal portion of the marker band for glue to seep through to better secure the marker band (shown as 694 in FIGS. 10 and 24), and/or use of a platinum ribbon or wire (e.g., 0.001 inch×0.003 inch×1–2 inches) looped back through one of the holes 694 located in the proximal portion of the marker band and glued to itself, with the proximal ribbon end glued between the inner and outer walls of the distal portion of the body of the device, preferably approximately at the junction of walls 382 and 384 of FIG. 7 or at the HDPE/LDPE outer wall junction of the alternate embodiment described. Addition of the platinum ribbon also appears to improve the "pushability" of the distal end of the device, which is desirable during treatment.

It has been discovered that the pushability—and thus, in part, the efficacy—of the embodiments disclosed herein, including the device shown in FIG. 10, are improved by taking advantage of an "over-the-wire" design. In other words, a construction is preferable that is capable of (i) tracking a guide wire through various body lumens to the site of the occlusive material to be treated and (ii) tracking back and forth, as necessary, over the wire during treatment, rather than simply relying on its own inherent stiffness to move across or through the occlusive material. The device depicted in FIG. 10, for example, preferably is used substantially as described for the device shown in FIGS. 2 and 5. More specifically, after a guide wire has been delivered to, and then across, the occlusion to be treated, the device (with lumen 680 mounted on the guide wire) is advanced along the guide wire through the occlusion, so that the active tip of the device is distal of the occlusion. The beveled section 692 aids the device to cross the occlusion by minimizing the surface presented to the clot as the device passes over the wire. To further aid the device to cross the clot, the shaft of the device may be strengthened by adding a mandrel extending distally to the active tip of the device. The device may be activated with the guide wire extended beyond the distal tip, or with the wire withdrawn. Withdrawing the wire may enhance the efficiency of clot removal. After the fibers are activated with high-frequency, low-energy pulses of radiation, as previously described, the device is slowly withdrawn through the occlusion, disrupting occlusive material in the process.

Although not yet fully understood, it appears that the embodiment shown in FIG. 10 is better able to disrupt occlusive material if flow is allowed to develop over longer periods of time than for the embodiments having both pumping and chewing optical fibers. For example, maintaining a duty cycle of 0.33, a first fiber in FIG. 10 preferably would fire consecutive pulses of radiation for about 100 cycles, and then "rest" for about 200 cycles, with the previously described frequency, energy per pulse, and wavelength, before the next fiber would fire. This compares to the embodiment shown in FIG. 9, for example, which might have its pumping fiber 514 fire, e.g., for about 20 consecutive pulses, with about 40 "rest" pulses, before firing would be shifted to each of the chewing fibers 516, the first of which might only fire for a few consecutive cycles of one or two active pulses and two or four "rest" pulses, before firing would be shifted to the next chewing fiber. By firing each fiber for an increased number of consecutive pulses, flow is able to develop, where flow might otherwise not develop with this embodiment.

FIG. 11 discloses a variation on the marker band shown in FIG. 10. In this embodiment, beveled section 696 includes bevel ports 698 and auxiliary ports 700. Each fiber and slot combination, as described for the marker band in FIG. 10, has a corresponding bevel port 698. Each bevel port may have any shape, from round to oval to elongated oval. The larger the port, the easier it is to align with the fiber 684. In any event, the combination of bevel port 698 and window 682 define a working edge 702 that causes disruption of the occlusive material during treatment as occlusive material is drawn into the apparatus through window 682 and/or bevel port 698. Since bevel 696 restricts flow somewhat when compared to flow generated through a marker band design lacking any bevel, optional auxiliary ports 700 help to provide additional flow through the distal tip of the device to provide better cooling of the beveled device.

FIG. 12 shows a device 900 for disrupting occlusive material in a body lumen, as previously described, according to another embodiment. Many aspects of this device are described in relation to other embodiments in this description, particularly in relation FIGS. 7 and 10, which aspects supplement the description of this particular device 900 in relation to FIG. 12.

For illustration purposes, the device 900 is shown (FIG. 12A) with its most proximal end housed in, and in operable communication with, a conventional introducing device 1000. The device 900 is an annular structure which extends along a longitudinal axis A. Along the length of the device 900 are various sections 902, 904, 906, 908 and 910, composed of different materials, as described below. In each of these sections, the annular structure of the device 900 is composed of concentric annular layers, composed of different materials, as further described below. The varied composition of the device 900, both longitudinally and in annular cross-section, give the device its desirable properties of strength and flexibility, where needed, for its intended purpose.

As shown in FIG. 12A, the device 900 has a most proximal section 902, the outermost annular layer of which is preferably composed of a composite of polyimide/spiral stainless-steel tubing, such as the Phelps-Dodge High-Performance Conductor tubing previously described in relation to FIG. 7A. This most proximal section 902 (shown abbreviated, for convenience) is approximately 95 cm in length and about 0.040 inch in OD. Adjacent this proximal section 902 is a middle section 904, the outermost annular layer of which is preferably composed of high-density polyethylene (HDPE). This middle section is about 47 cm long and has an OD of about 0.037 inch. Adjacent this middle section is a first distal section 906, the outermost annular layer of which is preferably composed of low-density polyethylene (LDPE). Adjacent this first distal section is second distal section 908, the outermost annular layer of which is preferably composed of plasticized polyvinylchloride (PVC) of 60–65 Shore A hardness. The first distal section 906 and the second distal section 908 have lengths of 5 cm and 3 cm, respectively, with both of these sections having an OD of about 0.035 inch, although ODs of from about 0.035 inch to about 0.040 inch have been used. Appended to the second distal section 908 is the distal-most section 910, which has a length of about 0.039 inch, an ID of about 0.034 inch, and an OD of about 0.038 inch. The various sections are joined at the junctions between 902 and 904, 906 and 908, and 908 and 910 with glue, and at the junction between 904 and 906 by melting, in ways previously described.

Preferably, a thermocouple wire 914 in the interior of the annular structure of the device 900 extends along most of the length of the device, terminating within the distal-most section 910 before the distal end 912 of the device. Preferably, this wire 914 extends along a side of the device, as shown, substantially parallel to, and offset, from the central longitudinal axis A. Preferably, this wire 914 is positioned between the outermost annular layers of the device described above and the innermost annular layers described below. This thermocouple wire 914 is also shown in FIG. 12C.

A platinum ribbon or wire 916 also lies within the interior of the device 900. The proximal end of the platinum ribbon is located at the junction between the middle section 904 and the first distal section 906. The platinum ribbon 916 continues along the length of the device into the distal-most section 910 until it reaches a hole 918 in the distal-most section. One or more of the holes 918 can be seen more clearly in FIGS. 12B and 12C. At this point, the platinum ribbon 916 is threaded through the hole 918 and glued to itself at a point proximal in relation to the hole, as previously described in relation to FIG. 10. Preferably, the platinum ribbon 916 extends along a side of the device, as shown in FIG. 12A, substantially parallel to, and offset, from the central longitudinal axis A, and opposite the thermocouple wire 914 described above. This ribbon 916 is preferably positioned between the outermost annular layers, described above, and the innermost annular layers of the device.

The innermost annular layers of the device 900 are now described. In the most proximal section 902 of the device, the innermost annular layer 903 is preferably composed of polypropylene and has an ID/OD of about 0.023/0.026 inch. This innermost annular layer 903 continues along the length of the device into the middle section 904, terminating at dotted line 905. At this juncture, the polypropylene layer is joined (using joining methods, such as gluing, as previously described) to an innermost annular layer 907 which is preferably composed of PVC and has an ID/OD of about 0.022/0.026 inch. This innermost annular layer of PVC continues along the length of the device, through the remainder of the middle section 904, through the first distal section 906, through the second distal section 908, and into the distal-most section 910, terminating therein at dotted line 911, as can be seen through the window 920, which is further described below. Within the innermost annular layer 907 lies a tube of polyimide 909 (shown in FIG. 12C) of about 0.039 inch in length, the distal end of which terminates at dotted line 911 (FIG. 12B) along with layer 907.

The device 900 is a variation of the "windowed" device shown in FIG. 10. The distal-most section 910 of the device 900 is a marker band having four windows 920, evenly spaced about 90 degrees apart, as shown in FIGS. 12B and 12C. The windows are preferably about 0.008 inch wide and 0.02 inch long, although shorter windows of about 0.005 inch have produced satisfactory results. One fiber 922 is positioned at each window 920. Within the device 900, each fiber 922 extends along the length of the device from its most proximal end to a point marked by dotted line 924, that is, at about three-quarters of the length of the window 920. Each fiber is positioned between the outermost annular layers and innermost annular layers described above, although the innermost annular layer in the distal-most section 910 of the device terminates at a point marked by dotted line 911, that is, at about one-half of the length of the window.

Preferably, the marker band 910 is about 0.038 inch in OD diameter and about 0.039 inch in length, although dimensions of from about 0.028 inch to about 0.042 inch in OD and from about 0.020 inch to about 0.060 inch in length have proved satisfactory. Within the marker band 910, the innermost annular layer has an ID of about 0.018 inch, although IDs of from about 0.018 inch to about 0.022 inch have proved effective. At a point 1 mm back from the distal end of the innermost annular layer, the ID of this layer increases to about 0.022, although IDs from about 0.018 inch to about 0.022 have proved effective. The innermost annular layer maintains this ID from this point to a proximal point at dotted line 905, where the ID increases to about 0.023 inch. The innermost annular layer maintains this inch ID from this proximal point to the proximal end of the device 900.

Preferably, the marker band section 910 is beveled at its distal end, as shown in FIGS. 12A–C, to facilitate movement through a vessel. The bevel 926 may begin at about 0.003 inch (dimension x) from the distal end 912 of the marker band section and have a bevel angle a (measured from the side of the device) of about 51.3 degrees. Further, the opening at the distal end 912 of the marker band lying between the innermost portions of the bevel may have a ID of about 0.028 inch (dimension y). The marker band section 910 may have holes (not shown) on the beveled portion thereof, such as the holes 698 of FIG. 11. In such a case, the holes would be smaller than the holes 698, for example, having diameters similar to that of the fibers 922. The holes could be formed manually, using a drill bit for example, although machining the holes is preferable to provide better uniformity and reproducibility.

The bevel 926 on the marker band section 910 facilitates movement of the device through the vessel while reducing or preventing damage to the vessel The bevel 926 may provide a further advantage. That is, as previously described in relation to FIG. 10, the device 900 may be delivered "over the wire". A wire or guide wire (typically, 0.014 inch in OD) provides greater maneuverability and safety, as one can push the device forward or pull it backward within a curved and branching vessel without undue concern about causing damage to the vessel wall. After delivery of the device 900 over the wire, a distal end of this wire or guide wire may be positioned beyond the distal end 912 of the device or fully housed within the device, when one or more of the optical fibers 922 are energized. Preferably, the distal end of the guide wire is positioned within the device, as described further below. However, when the guide wire 929 extends beyond the distal end 912 of the device, as schematically illustrated in FIG. 12E, it is relatively free to move about beyond the distal end 912. If completely unconstrained, the distal end of the guide wire 929 might move in front of the optical fiber and thereby be irradiated by the radiation 930 emitted from an optical fiber 922. Such a result is undesirable, as a heated guide wire may damage the vessel. The bevel 926 prevents this undesirable result by preventing the extended distal end of the guide wire 929 from moving in front of an optical fiber 922 where it might otherwise be irradiated. Positioning of the guide wire 929 and the device 900 is further described below in relation to the operation of the device.

An embodiment of the device is now described in relation to FIG. 12D, which shows section 906 of the device 900. In this embodiment, holes 928 extending through both the outermost and innermost annular layers are placed in the first distal section 906 of the device. Preferably, six such holes 928 are used, although anywhere from one to about 15 holes may be used. The holes 928 may be arranged in three sets along the length of the first distal section 906, each set having two holes positioned along an annular portion of section 906. For each set, the two holes may be spaced 180 degrees apart and offset 90 degrees from the location of the thermocouple wire 914 and the platinum ribbon 916. In FIG. 12D, only one hole of each set can be seen, the other hole being located on the other (non-visible) side of the device. While an arrangement of six holes has been described, other arrangements are possible, particularly if a different number of holes is used. For example, if 15 holes are used, they may be arranged in five sets along the length of the first distal section 906, each set having three holes, evenly spaced 120° apart along an annular portion of section 906.

Preferably, the holes are 0.011 inch in diameter, although diameters of about 0.005 inch to about 0.012 inch are possible, as are oval dimensions of from about 0.003 inch by about 0.005 inch, to about 0.003 by about 0.011 inch, or to about 0.011 inch by about 0.39 inch. The most proximal set of holes is placed about 5 cm proximal from the distal end 912 of the device, while the middle set of holes and the distal-most set of holes are placed about 4 cm and 3 cm, respectively, from the distal end 912 of the device.

It is believed that the holes used in this embodiment provide advantageous fluid flow when the device is employed as described in relation to FIG. 10. That is, a device such as device 900 is pushed through an occlusion 362 (FIG. 5) preferably with the aid of a guide wire 929, a bevel 926 on the distal end 912 of the device, and a conventional lubricious or hydrophilic coating on the outside of the device 900. Once the device is desirably placed with the active tip of the device distal of the occlusion, the optical fibers 922 are activated and the tip of the device is pulled back through the occlusion. This causes occlusive material to be sucked into the distal end 912 of the device and expelled through the windows 920. However, when the tip of the device is pulled through the occlusion, there may be loss of fluid or blood at the tip which inhibits the functioning of the device. It is believed that the blood flowing into the holes 928 at a relatively high pressure section of the device and exiting the relatively low pressure tip of the device remedy this problem.

When the device 900 of FIG. 12D is used with the guide wire located proximally of the distal end 912 (not shown) and the holes 928, the blood flow may be on the order of about 6 cm$^3$ in 60 seconds (about 6 cc/min). When that same device is used with the guide wire extending beyond the holes 928, such as beyond the distal end 912 as shown in FIG. 12E, the blood flow through the 6 holes, arranged and sized as shown and described above, may be on the order of about 1 cm$^3$ in 60 seconds. Such flows provide sufficient fluid to the distal tip 912 of the device to maintain proper functioning of the device 900.

As described previously, the device 900 produces pressure waves which assist in the breaking up of clot material. The device also and primarily acts as a fluid dynamic device, utilizing the asymmetry of the structure to produce net fluid flow and clot-destructive forces, as described further below. The device produces macroscopic fluid motion which serves to move the clot material or occlusive material around to maximize the amount of material passing in the vicinity of the functional area of marker band section 910 of the device.

Preferably, the device 900 has four windows 920 and four optical fibers 922, as shown and described above. A device with fewer windows/fibers could be produced more easily, although with such a device there is a concern if one or more of the windows became somehow blocked, or positioned against the vessel wall, there would be an insufficient number of active windows for efficient functioning of the device. It is believed that with a device 900 having four windows/fibers, two of the windows should almost always be unobstructed to provide for proper functioning of the device. A device 900 having greater than four windows/fibers could also be used.

The preferred method of operating the device 900 is now described. The proximal ends of the optical fibers 922 are operably connected to an energy source (not shown), which is preferably a laser which produces radiation that is well absorbed in blood and poorly absorbed in the wall tissue of the vessel. A preferred wavelength is about 414 nm, although such wavelengths may be hard to produce and lasers producing such wavelengths may be difficult to obtain on a commercially practical basis. A suitable wavelength is about 532 nm, as this wavelength is well absorbed in blood, having an absorption coefficient ($\alpha$) of from about 240 cm$^{-1}$ to about 270 cm$^{1-1}$ for this wavelength, while being poorly absorbed in the wall tissue of the vessel. One laser producing the desired wavelength is a doubled Nd:YAG laser.

The laser may be pulsed at about 5 kHz, using a pulse width of about 25 nanoseconds. The energy supplied by the laser may be up to about 500 $\mu$J. Typically, laser energy of about 200 $\mu$J is delivered from a 50 $\mu$J fiber, an amount sufficient to produce vapor bubbles in the vessel fluid. In order to manage the power (up to about 1 W) of the laser, which, if not managed appropriately, would be too high for a 1–3 mm vessel, the laser is cycled through "on" and "off" phases. A duty cycle of about 30%, which produces an average laser power of about 300 mW, can be used to reduce the total power delivered to the vessel. For example, for a particular fiber 922, the laser power may be cycled through an "on" phase of 100 pulses and an "off" phase of 200 pulses (providing a duty cycle of about 33%), with the pulses being separated in time by 200 $\mu$seconds. The above-described parameters produce good results, although it has been discovered that higher energy or power parameters may be employed, particularly if active cooling is used, as described in greater detail with respect to the embodiments of FIGS. 15–21.

Other parameters (such as fiber diameter and pulse repetition pattern) may also be selected to produce desired or optimal fluid mechanics and clot emulsification efficiency. Operational parameters may be chosen upon consideration of fluid viscosity and heat build-up within the fluid. For example, when the fluid is relatively viscous (for example, about 4 cP), a greater number of pulses in the "on" phase may be desired to get the fluid moving. However, any temptation to increase the number of "on" pulses, should be checked by a consideration of how much heat build-up in fluid is acceptable to avoid damage to the vessel wall. Preferably, a thermocouple 914 is used to measure the temperature of the fluid, and preferably, to control the applied laser power in a feedback control loop. Preferably, any such feedback control loop operates automatically, such as via a microprocessor or computer or other conventional means (not shown).

When the device 900 is operated as just described, the desired motion of the fluid therethrough is obtained. This fluid motion is schematically illustrated in FIG. 13 over a period of from zero to 100 $\mu$seconds. For example, FIG. 13A shows the initial activation of the device 900, wherein energy is deposited at the tip of an optical fiber 922 located adjacent window 920. As the "on" cycle continues, this deposition of energy causes a vapor bubble 940 to form and expand, as shown in FIGS. 13B and 13C, until the bubble collapses at about 60 $\mu$seconds, as shown in FIG. 13D. As shown particularly in FIGS. 13B–D, the bubble is expanding and collapsing in an asymmetric environment, that is, in an environment confined by asymmetric structure of the marker band section 910.

The asymmetric structure of the marker band results from one or more of its structural components, such as the distal opening 912, the bevel 926 (if bevel option employed) or other corner structure, the marker band wall, and the window 920. Other asymmetric structures and structural components are possible, the choice often depending on a variety of functional, practical and/or safety concerns. For example, an asymmetric marker band structure which employs a corner structure other than the bevel 926 provides a good asymmetric environment for bubble expansion and collapse and resulting fluid movement, but is not considered the safest option.

The expansion and collapse of the bubble in proximity to the asymmetric marker band structure 910 of the device causes a net fluid displacement in the vicinity of the fiber tip, which in turn causes net fluid displacement 942 directed outwardly from the window 920, as shown in FIG. 13E. A rebound phenomenon 944 may also occur at the fiber tip, as shown in FIG. 13F. In this manner, fluid in the vessel is moved mainly from the vicinity of the distal opening 912 of the device, through that opening and outwardly from the window 920 for a desirable directional displacement of fluid from the device 900. As described above, a single fiber 922 may be energized for 100 "on" pulses, followed by a rest for 200 "off" pulses, before another fiber 922 is cycled in this manner.

When the device 900 has been operated for many pulses, vigorous fluid motion, as schematically shown in FIG. 14 over a period of from zero to 60 mseconds, is obtained. For example, after many of 100 "on" pulses have been delivered to an optical fiber 922, a train 946 of net fluid displacements 942 is produced, as shown in FIG. 14A. Once the 100 "on" pulses have been delivered, and the fiber is in its rest phase for 200 "off" pulses, the train 946 of fluid moves further outwardly from the window 920, as shown in FIG. 14B. On a macroscopic level, the net fluid displacement is observed as a jet 948 of fluid being expelled from the window of the device 900, as shown in FIG. 14C. Once one duty cycle has run its course, resulting in the jet of fluid just described, the cycle is reproduced at another fiber 922. The firing pattern or schedule (i.e., firing of adjacent fibers, opposite fibers, or any combination of fibers, sequentially) may be selected according to the application (for example, according to the nature or position of the occlusion, or according to the heat build-up occurring in a particular region in the vessel, etc.). The repeated asymmetric jetting of fluid proximal to the distal tip 912 of the device and outward at various windows 920, according to a selected firing pattern, causes considerable material agitation in the vicinity of the tip and significant motion of the tip. Thus, the firing of the optical fibers 922 arranged in the device 900 provides a very effective fluid emulsification process.

When using the device 900, it is preferable to extend a guide wire 929 through the occlusion at the outset and then push the device 900 along the guide wire until the distal end 912 is distal of the occlusion. The guide wire may be of a particularly desired shape, or may be shapable, to influence the position of the device and/or the motion of the device traveling over the guide wire. Preferably, the guide wire is then withdrawn into the device 900, proximal to any flow holes 928 (FIG. 12D) that may be employed, so as not to interfere with the flow of fluid therethrough. The device 900 is then activated by supplying energy to one or more of the optical fibers 922, as described above, during which the distal end 912 of the device is pulled back (proximally) into the occlusion. After the device has been pulled back through the occlusion ("one pass"), the process is repeated, with another extending of the guide wire 929 through the occlusion. This method of operation is the most effective in terms of emulsification and the best in terms of heat management, in view of the internal position of the guide wire during activation.

It will be appreciated that there may be times when the positioning and repositioning process just described is difficult or is not as safe as desired. For example, when a vessel has many branches, after the initial positioning of the guide wire, it may be difficult to reposition the wire as it was initially positioned, given the number of branches present. Further by way of example, when a vessel is tortuous or convoluted, repeatedly extending the guide wire through the occlusion may threaten the safety of that vessel. Thus, it is possible to extend the guide wire through the occlusion initially, to push the device 900 along the guide wire until the distal end 912 is distal of the occlusion, and to leave the guide wire extended distal of the distal end 912 of the device. The device 900 may then be activated and pulled back over the guide wire, while the guide wire remains in place. After one pass of the device, the device may be repositioned by extending it again over the guide wire and the process may be repeated for additional passes. This method of operation is acceptable, although less effective in terms of emulsification and less optimal in terms of heat management than the preferred method described above.

There is yet another method of operation that may be used, although this method is the least preferred, as having relatively lower emulsification efficiency and heat management capability. According to this method, the guide wire is extended distal of the occlusion and the device 900 is activated as it is pushed forward (distally) along the guide wire into the occlusion. Generally speaking, in order to protect the vessel wall when the device is being pushed distally, it should only be pushed along a guide wire, with the guide wire remaining distal of the distal end of the device.

For the treatment of particularly small vessels less than about 2 mm in inner diameter, devices approaching 1 French dimensions (or smaller) have been constructed. Such devices can be thought of as "active wires": "wires" in the sense that the device is small enough to be deliverable through a guide catheter rather than over a guide wire (the typical manner of delivery of larger catheter devices) and/or is roughly no larger in diameter than a typical guide wire; and "active" in the sense that although these devices are only roughly wire-sized, each is capable of delivering optoacoustic energy to a treatment site. Many different constructions of an "active wire" are possible, as disclosed in the above-mentioned Ser. No. 09/165,435 application.

A variation of the device 900 of FIG. 12, according to a particularly preferred embodiment of the invention, is now described. According to this embodiment, a distal-most section 11 shown in FIG. 15A replaces the distal-most section 910 of the device 900 previously described. This distal-most section 11 includes a "window" portion 21 that is preferably a marker band having four windows 13, preferably evenly spaced about 90 degrees apart, as shown. Preferably, the window portion is a marker band of less than 100% platinum, such as about 90% platinum and about 10% iridium, to provide adequate hardness and mechanical strength. Further, preferably, the window portion has a wall thickness of desirable mechanical strength, such as about 0.002 inch. Preferably, an optical fiber 15 is positioned at each window, either with its distal end substantially flush with the proximal end of the window 13, as shown, or with its distal end adjacent a point between the proximal end and the distal end of the window 13. These fibers function as emulsifying or chewing fibers, as during operation they emulsify material located in the vicinity of their distal ends. The optical fibers 15 may be secured by glue applied to glue windows 17, such as by placing the optical fiber in a desired position relative to the window 13, applying glue such that it contacts the optical fiber 15 and fills the window 17, and allowing the glue to set or dry.

The distal-most section 11 also includes a distal extension or pump tube 23 that is secured, by any sufficient means, to the distal end 19 of the window portion 21. Preferably, the proximal end of the distal extension 23 is placed within the distal end 19 of the window section 21 such that the distal end 19 overlaps the proximal end of the distal extension 23. The overlap should be sufficient to facilitate maintaining the end of the distal extension within the end of the window section, such as an overlap of about 0.02 inch. When placed appropriately, the distal extension 23 and the window section 21 are joined, such as by soldering the two together along a seam formed therebetween, as is preferred. The distal extension 23 has a recession or groove 25 for accepting the distal end of an optical fiber 27, as shown. When the distal end of the optical fiber 27 is placed in the groove 25, as shown, it is prevented from interfering with a guide wire that may be located within the distal-most section 11, such as the guide wire 929 of FIG. 12E. This renders unnecessary the protective use of a bevel, such as the protective use of the bevel 926 of FIG. 12E described above, although a bevel 22 is still preferred to guide the guide wire smoothly from the window portion 21 into the pump tube 23. The optical fiber 27 may be secured along at least a portion of the inside wall of the window portion 21, using an adhesive or other suitable means, to facilitate its retention in an appropriate position.

Optical fiber 27 is a pumping fiber, as during operation it brings about fluid mechanics that attract occlusive material to the optical fibers 15. By way of explanation, the pumping fiber 27 pumps fluid from the vicinity of the windows 13 and coolant supplied to the distal-most portion 11 (as described below) in such a way that occlusive material is attracted to the vicinity of the windows 13 and further into the windows 13 to the vicinity of the optical fibers 15 for emulsification. The distal-most section 11 may also include bars 35 that separate windows 13 from further windows 37, as shown in FIG. 15C. These bars are positioned adjacent a point between the distal ends of the optical fibers 15 and the distal ends of the windows 37. The bars 35 are emulsifying or chewing bars, as during operation they serve as a mechanical aids in emulsifying material in the vicinity of the windows.

The distal-most section 11 may be secured to a device such as device 900 of FIG. 12 in the same manner as the distal-most section 910 may be secured to that device, as described above, for example, via holes 33 in the distal-most section 11, or by any other sufficient means, such as by an outer annular tube 31 (the length of which is only partially shown) abutting and attached to, or glued to, window portion 21. When fully assembled, the device may be used for emulsifying clot material, as previously described. Further, the device may be very effectively used for such applications when cooling fluid is supplied via the introducing device 1000 to the central lumen of the device, as further described below.

A variation of the distal-most section 11 of FIG. 15 is now described in relation to FIG. 16. According to this variation, an innermost annular layer 39 lies within the interior of the device and an inner lumen 41, typically of polyimide, lies within the innermost annular layer 39. These layers are simply those previously described as the innermost annular layer 903 (proximal) and 907 (distal) and the tube 909, respectively, in the device 900 of FIG. 12.

FIG. 17 shows a variation to the distal-most section 11 of FIGS. 15 and 16 described above. According to this variation, the optical fibers 15 are secured to the distal-most section 11 not by adhesion, but by tabs 43 located in windows 13; as shown. Preferably, the tabs 43 secure the fibers 15 such that their distal ends are proximal of chew bars 35, such as those described in relation to FIG. 15C above. In this variation, the window portion 21 preferably has an appropriate aspect ratio relative to the size of the fiber 15, such as a wall thickness about 0.001 inch when a 50/55/63 fiber is used. Further, preferably the window portion 21 s a marker band of less than 90% platinum, such as about 80% platinum and about 20% iridium, to provide adequate hardness and mechanical strength. As also shown in this variation, the distal-most section 11 may be a unified combination of the window section 21 and the distal extension 23 described above. Further, the distal-most section may be of a shape, such as a shape having a substantially smooth external profile, sufficient to facilitate access to the obstruction in the vessel while minimizing injury or damage to the vessel wall.

FIG. 18 shows another variation of the distal-most section 11 of FIGS. 15–17 described above, shown merely by way of convenience without the distal extension 23. According to this variation, the optical fibers 15 are secured to the distal-most section 11 not by adhesion or tabs, but by tubes 45 disposed on a ring 47 in a manner that corresponds to the desired location of the optical fibers within the window portion 21 of the distal-most section 11. During assembly, the optical fibers 15 are threaded through the tubes 45, as shown in FIGS. 18A and 18B. When the optical fibers 15 are suitably positioned within the tubes 45, such as at the position shown in FIG. 18B, the fibers are secured or glued in that position, such as by applying glue at the proximal ends of the tubes 45. A window portion 21 is aligned with the ring 47 that carries the tubes 45, such that the windows 13 thereof are aligned with the tubes. 45 and thus the optical fibers 15 positioned therein. While the window portion 21 is shown as fitting within the ring 47, any suitable means of aligning the ring and the window portion may be used, such as fitting a smaller ring within a larger window portion. The circular holes 33 and 49, on the window portion 21 and the ring 47, respectively, are glue holes that may be used to secure various parts of the device relative to one another during assembly. When the optical fibers are aligned with the windows in a desirable configuration, such as that shown in FIG. 18B, the window portion 21 is combined with the distal extension 23 in any suitable manner to form the distal-most section 11 described above.

It is presently preferred to provide one pumping fiber and four chewing fibers, as shown and described in relation to FIGS. 15–18, for a distal-most section 11 of the size contemplated for accommodating optical fibers having a core diameter of about 50 microns, such as 50/55/63 or 50/55/65 fibers. By way of example, the window portion 21 of such a distal-most section 11 may have an outer diameter of about 0.036 inch. For a larger device 11, it is presently preferred to provide one pumping fiber and four or more chewing fibers. Smaller devices 11 are contemplated, such as devices about half the size of that described above or less, to the extent construction is practicable and operation is useful. The number of pumping and chewing fibers (as well as the corresponding windows) may be varied (for example, from one of each, upwards) according to the desired size of the device, according to the desired result to be achieved from use of the device, or according to the nature of the obstruction to be disrupted from use of the device.

The device 900 as modified with the distal-most portion 11 just described (hereinafter, sometimes referred to as the "modified device"), may be operated much as described previously in relation to the device 900 of FIG. 12. As with all embodiments of the invention, the laser parameters, such as the pulse duration, the pulse frequency, the wavelength, the pulse energy, and the power, and the like, may be varied while still producing the desired phenomena. By way of example, it is possible to use a pulse duration of between about 5 and about 30 ns, such as 25 ns; a pulse frequency of from about 1 to about 10 kHz, such as about 5 kHz; an energy per pulse of about 100 to about 500 $\mu$J, such as about 300 $\mu$J; a power of about 0.5 to about 2 W, such as about 1.5 W, where a duty cycle of from about 50% to about 90%, such as about 80% (for example, 240 pulses "on" and 60 pulses "off"), or from about 50% to about 75%, such as about 66.7% (for example, 200 pulses "on" and 100 pulses "off"), is used to arrive at an average power of from about 0.5 or 0.75 to about 1.5 W, such as 1.0 W; provided appropriate cooling, such as the active cooling further described herein, is used to manage the heat within the vessel to minimize or prevent damage to the vessel wall. In a preferred embodiment, the pulse frequency is set, such as at a level of about 5 kHz, the energy per pulse is selected, such as an energy per pulse of about 300 $\mu$J, and a duty cycle is selected, such as a duty cycle of about 66.7%, to obtain a desirable average power at the distal end of the device 900.

Active cooling may include providing a biocompatible coolant within a lumen of the various devices described herein, such as device 900 of FIG. 12 or the modified device of FIGS. 15–18, using a coolant flow rate of from about 0.5 cc/min, such as from about 0.5 to about 3 cc/min, or preferably about 1 cc/min, wherein the coolant has suitable viscosity and radiation-absorption characteristics, as further described herein. The biocompatible coolant can be supplied to the vessel via an introducer, such as the introducer 1000 (FIG. 12) of any of these devices. When a coolant is actively provided, it is preferable not to use the passive cooling means of holes 928 described above in relation to FIG. 12D.

A suitable coolant is blood, or another radiation-absorbing fluid, such as a dye-based fluid. By way of example, a suitable dye-based fluid is based on Indigo Carmine, such as that commercially available from Hope Pharmaceuticals of Scottsdale, Ariz. It is preferable to use a coolant with the highest possible radiation-absorbing characteristics, so that a lower level of radiation energy or power, could be used. Blood has an absorption coefficient of about 240 cm$^{-1}$, to about 270 cm$^{-1}$ for radiation having a wavelength of about 532 nm. The coolant may have an absorption coefficient in a range of about 170 cm$^{-1}$ to about 300 cm$^{-1}$ for the radiation of the same wavelength. While the foregoing has been described in terms of a radiation wavelength of 532 nm, other wavelengths (such as 414 nm) may be used, such as a wavelength corresponding to the absorption peak for a particular coolant or dye, a limitation typically being the availability of a suitable source of radiation of such wavelength. It is also preferable to use a coolant with the lowest possible viscosity to facilitate its delivery to the vessel and to provide effective fluid dynamics. The viscosity of blood is about 4 cP. The coolant may have a viscosity of from about 0.5 cP to about 4 cP, such as about 1 cP. In the selection of a suitable or preferred coolant, it may be necessary to balance the radiation-absorbing and viscosity characteristics of various coolants, arriving at some compromise therebetween, given the availability of suitable radiation sources and biocompatible coolants.

The various operational parameters described above may be varied according to the properties of the selected coolant or according to other considerations or constraints. For example, the duty cycle may be other than that provided above (which is particularly suitable when the coolant is blood), depending on the viscosity or other characteristics of the coolant. By way of example, if the viscosity of the coolant is lower than that of blood, a duty cycle of 100 pulses "on" and 50 pulses "off" might be used. Further by way of example, the level of power used may be varied, such as to the highest level possible without causing any substantial injury or damage to the vessel wall. By way of example, substantial injury or damage to the vessel wall refers to perforation of the vessel wall or necrosis of tissue of the vessel wall. The limit on the power level is generally the amount of cooling provided. The level of radiation energy delivered by the fibers may also be varied, such as to the highest level possible that avoids damage to the optical fibers and avoids substantial damage to the vessel wall.

As described above, the distal-most section 11 of FIGS. 15–18 is a substitute for the distal-most section 910 of the device 900 of FIG. 12. The resulting modified device 900 may be advanced toward the proximal portion of the occlusion as previously described in relation to FIG. 5. Preferably, the modified device 900 is used in the manner described for the device of FIGS. 2 and 3 in relation to FIG. 5, and in some ways in the manner described for the device 900 of FIG. 12. By way of explanation, the modified device 900 is preferably pushed through an occlusion 362, preferably with the aid of a wire, such as the guide wire 929 of FIG. 12E, and a conventional lubricious or hydrophilic coating on the outside of the device 900. Once the device is desirably placed with the active tip of the device, including the distal-most portion 11, distal of the occlusion, the guide wire is removed from the active tip of the device, and preferably, entirely from the device 900, such that it does not interfere with the flow of coolant through the device. The coolant is then provided within the device, such as by way of the introducer 1000, to produce a coolant flow in the distal-most portion 11 of the device 900. The optical fibers 27 and 15 are fired and the active tip of the device is pulled back through the occlusion 362. While the pump fiber 27 may be fired before the initial firing of any of the optical fibers 15, this order is not necessary. Preferably, the firing cycle consists of an initial firing of the pump fiber 27, followed a firing of each of the chew fibers 15 in succession, which firing cycle may be repeated as many times as necessary to obtain the desired results.

The pump fiber draws material from the vicinity of the windows 13 in a pathway towards the pump tube 23. The chew fibers emulsify the material in the vicinity of their distal tips along this pathway. Material reaching the pump tube 23 is then expelled through the windows 13 and/or through the distal end 29 of the pump tube 23, although the net fluid motion over a firing cycle is through the distal end of the pump tube. Preferably, a thermocouple, such as thermocouple 914 of FIG. 12, is disposed within the distal-most portion 11 of the modified device 900 to monitor the temperature therein. If the temperature indicates that damage to the vessel wall is likely, the physician can take steps to reduce the temperature, such as by interrupting further radiation delivery, adjusting the flow of coolant, or adjusting the energy level, the power level, the duty cycle, or other operational parameters. Of course, as described previously, automated feedback control may be used.

When the modified device 900 is operated as just described, the desired motion of material or fluid in relation to the device is obtained. The fluid motion resulting from operation of the pump fiber 27 is schematically illustrated in FIG. 20 over a period of from zero to about 80 $\mu$seconds. For example, FIG. 20A shows the initial activation of the device 900, wherein energy is deposited at the tip of a pump fiber 27 located in groove 25 of the pump tube 23. As the "on" cycle continues, this deposition of energy causes a vapor bubble 51 to form and expand, as shown in FIGS. 20B, 20C and 20D, until the bubble collapses, as shown in FIGS. 20E, 20F, 20G and 20H.

As shown particularly in FIGS. 20B–G, the bubble 51 is expanding and collapsing in an asymmetric environment, that is, in an environment confined by asymmetric structure of the distal-most portion 11 of the modified device 900. The asymmetric structure of the distal-most portion 11 results from one or more of its structural components, such as the distal opening 29, the bevel 22 (if bevel option employed) or other corner structure, the walls of the pump tube 23 and the window portion 21, the windows 13, and the position of the pump fiber 27 within the distal-most portion 11 of the device. Other asymmetric structures and structural components are possible, the choice often depending on a variety of functional, practical and/or safety concerns.

The expansion of the bubble 51 within the pump tube 23 causes a net fluid displacement in the vicinity of the tip of the optical fiber 27, which in turn causes net fluid displacement directed outwardly from the windows 13 and, more predominantly, from the distal end 29 of the pump tube 23, as shown in FIGS. 20C and 20D. The collapse of the bubble within the pump tube 23 causes a net fluid displacement directed toward the distal end of the pump tube 23, as shown in FIGS. 20E, 20F and 20G. While the space once occupied by the bubble is filled with fluid coming from the windows 13 and from the distal end 29 of the pump tube 23 when the bubble collapses, most of this fluid comes from the windows 13 of the window portion 21. As described above, the pump fiber 27 may be energized for a number of "on" pulses, such as 200, followed by a rest for number of "off" pulses, such as 100, before it is cycled again in this manner.

The fluid motion resulting from operation of one of the chew fibers 15 of the modified device 900 is schematically illustrated in FIG. 21 over a period of from zero to about 80 μseconds. For example, FIG. 21A shows the initial activation of the modified device 900, wherein energy is deposited at the tip of a chew fiber 15 located in a vicinity of one of the windows 13 of the distal-most portion 11 of the device. As the "on" cycle continues, this deposition of energy causes a vapor bubble 53 to form and expand, as shown in FIGS. 21B, 21C and 21D, until the bubble collapses, as shown in FIGS. 21E, 21F, 21G and 21H. The bubble 53 is expanding and collapsing in an asymmetric environment, that is, in an environment confined by asymmetric structure of the distal-most portion 11 of the modified device 900, as described above in relation to bubble 51.

The expansion of the bubble 53 at the distal end of the chew fiber 15 adjacent the window 13 causes a net fluid displacement away from the tip of the optical fiber 15, which in turn causes net fluid displacement directed away from the window 13, as shown in FIGS. 21B, 21C and 21D. The collapse of the bubble at the distal end of the chew fiber 15 causes a net fluid displacement directed toward the distal end of the chew fiber 15, as shown in FIGS. 21E, 21F, 21G and 21H. The expansion and collapse of the bubble 53 just described causes a net displacement of fluid out of the window 13. This is similar to the effect described above for the device 900 of FIG. 12 in relation to FIGS. 13 and 14. A distinction lies in the fact that the device 900 of FIG. 12 is optimized for this fluid displacement, while the modified device 900 shown in FIG. 21 is optimized more for clot emulsification than for fluid displacement. Thus, the displacement of fluid out of the window 13 of the modified device 900 of FIG. 21 is more incidental than is the fluid displacement associated with a window of device 900 of FIG. 12. In the modified device 900, per pulse of energy, the net fluid displacement out of the window 13 caused by chew fiber 15 is substantially less than the net fluid displacement out of the distal end 29 of the pump tube 23 caused by the pump fiber 27.

As described above, the chew fiber 15 may be energized for a number of "on" pulses, such as 200, followed by a rest for number of "off" pulses, such as 100, before another chew fiber 15 is cycled in this manner. The firing pattern or schedule for the chew fibers 15 (i.e., firing of adjacent fibers, opposite fibers, or any combination of fibers, sequentially) may be selected according to the application (for example, according to the nature or position of the occlusion, or according to the heat build-up occurring in a particular region in the vessel, etc.). As described above, a typical firing cycle consists of initially firing the pump fiber 27 and subsequently firing each of the chew fibers 15 in succession, which firing cycle may be repeated to obtain the desired results. When such a firing cycle is employed, it is the pump fiber 27 the dominates over the chew fibers 15 with respect to the fluid motion caused by operation of the modified device 900. For example, even though the pump fiber 27 is preferably cycled once for every cycling of one or more chew fibers 15 in a typical firing cycle, the pump fiber 27 dominates such that the net fluid displacement is greater at the pump tube 23 than it is at the window portion 21 of the distal-most section 11.

The repeated pumping of fluid via the pump fiber 27 and chewing of the occlusive material via the chew fibers 15, according to a selected firing pattern, causes considerable material agitation in the vicinity of the distal tip of the apparatus and significant motion of the distal tip. Thus, the firing of the optical fiber 27 and the optical fibers 15 arranged in the modified device 900 provides a very effective fluid emulsification process. When the modified device 900 has been operated for many pulses, vigorous fluid motion is obtained and the occlusive material is disrupted or emulsified toward dissolution.

The device 900, as modified with the distal-most section 11 of FIGS. 15–18, operates much more effectively than the unmodified device 900 of FIG. 12. By way of example, FIG. 19 shows the results of a test carried out using the unmodified device 900 of FIG. 12, referred to as Device A, operating at average power levels of about 0.33 W, 0.50 W, and 1.00 W, and a modified device 900, referred to as Device B, operating at an average power level of about 1.00 W. Device B included a distal-most section 11 similar to that of FIG. 16A, although lacking the optional glue windows 17. Devices A and B were tested to determine the rate of clot dissolution when operated within a curved tube containing porcine clot, ex vivo. The clot was aged variously from one to seven days, cut into about 1 cm sections, weighed, and placed in the tube. The tube had an inner diameter of about 3 mm, to approximate a human vessel, and the clot filled this diameter at a point along the length of the tube. The section of tube containing the clot was curved over a mandrel having a diameter of 0.50 inch to create a curve radius at the inner tube wall, nearest the mandrel, of about 0.25 inch.

In the test, the distal end of the test device was inserted into the tube such that it followed along the curve of the outer tube wall, furthest from the mandrel, and was pushed through the clot as described previously. The distal end of the device was thus forced against the outer tube wall to test its ability to attract the clot from the inner tube wall, as well as its ability to emulsify or dissolve the clot. During operation of the device, coolant was supplied from the distal end of the device to the tube, and the distal end of the device was then pulled back through the clot during radiation exposure, as previously described. The device was operated using the parameters set forth in Table 1 below; laser radiation of a wavelength of 532 nm; and a blood-analog coolant, including a red amaranth dye, having a viscosity of about 4 cP and an absorption coefficient of about 270 $cm^{-1}$ for radiation of a wavelength of 532 nm, and exhibiting non-Newtonian fluid behavior, delivered through the inner lumen of the device via a syringe pump at a flow rate of about 1 cc/min. The blood-analog coolant consisted of about 1.080 milliliters of $H_2O$, about 9 grams of NaCl, about 720 milliliters of glycerin, about 780 milligrams of Xanthan gum, and about 5.4 grams of amaranth dye, resulting in about 1.8 liters of the 4 cP blood-analog coolant. (See Brookshier, K. A., et al., *Evaluation of a Transparent Blood Analog Fluid: Aqueous Zanthan Gum/Glycerinol*, Biorheology 30, 107–116 (1993), regarding blood analog fluid.)

TABLE 1

OPERATIONAL PARAMETERS

| Device | Energy | Pulse Frequency | Number of Pulses On | Number of Pulses Off | Duty Cycle | Average Power |
|---|---|---|---|---|---|---|
| A | 250 µJ | 5 kHz | 80 | 220 | 26.7% | 0.33 W |
| A | 300 µJ | 5 kHz | 100 | 200 | 33.3% | 0.50 W |
| A | 300 µJ | 5 kHz | 200 | 100 | 66.7% | 1.00 W |
| B | 300 µJ | 5 kHz | 200 | 100 | 66.7% | 1.00 W |

For each device, the time taken to dissolve the clot completely was measured. The clot dissolution rate, in grams per minute, was calculated from the time measurement and charted in the bar graph of FIG. 19. As shown in FIG. 19, Device A provided a dissolution rate of about 0.01 gram per minute when operated at an average power of about 0.33 W; about 0.014 gram per minute when operated at an average power of about 0.50 W; and about 0.02 gram per minute when operated at an average power of about 1.00 W. As also shown, Device B provided a dissolution rate of about 0.035 gram per minute when operated at an average power of about 1.00 W. Device B thus performed about 175% better than Device A, when operated at an average power of about 1.00 W.

A similar test was conducted with Device B, using a red-dye coolant having a viscosity of about 1 cP, in place of the 4 cP blood-analog coolant described above, and operating at an average power of about 1.00 W. The 1 cP red-dye coolant consisted of $H_2O$, NaCl, and amaranth dye, lacking the glycerin and Xanthan gum components of the 4 cP blood-analog coolant described above. The 1 cP red-dye coolant had about the same absorption characteristics as the 4 cP blood-analog coolant. In this test, the combination of Device B and the 1 cP red-dye coolant provided a dissolution rate of about 200% greater than that provided by the combination of Device B and the 4 cP blood-analog coolant. Note that it is unlikely that either the red-dye coolant or the blood-analog coolant just described would be used in practice, as it is not clear whether or not these coolants are biocompatible. Nonetheless, each of these coolants is believed to be a good model for a biocompatible coolant suitable for use in practice of the invention.

A similar test was also conducted with Device B, using a blue-dye coolant, including Indigo Carmine dye and $H_2O$, having a viscosity of about 1 cP and an absorption coefficient of about 170 $cm^{-1}$ for a radiation wavelength of 532 nm, and operating at an average power of about 1.00 W. In this test, the combination of Device B and the 1 cP blue-dye coolant provided a dissolution rate of even more than 200% greater than that provided by the combination of Device B and the 1 cP red-dye coolant. The blue-dye coolant just described is biocompatible and suitable for use in vivo.

The present invention provides advantageous apparatus and methods of disrupting occlusive material in a body lumen at relatively high power levels, while managing heat within the lumen to avoid substantial thermal damage to the lumen tissue. When a relatively high average power such as from about 0.75 W to about 1.5 W is used, according to the present invention, effective disruption of occlusive material is obtained. Heat management is obtained by cycling the radiation energy through "on" and "off" periods to bring the average power delivered to the lumen to an acceptable level and/or by providing active cooling to minimize undesirable thermal conditions at the lumen tissue. The present invention thus provides apparatus and methods of disrupting occlusive material in body lumens, particularly blood vessels, in an acceptably safe and effective manner.

While the foregoing has described preferred illustrative embodiments of the invention, other embodiments of the invention are possible. Further, while the context in which the invention has been explained concerns addressing a partial or total occlusion of a human vessel, the present invention, including its pumping/sucking/chewing aspects, has application beyond the human body to any context in which it is practical to move fluid from one location to another using radiation energy. Additionally, while certain materials of construction have been identified herein, the invention is not particularly dependent upon the types of materials used. While various structures are shown in this disclosure as being part of a marker band versus the body sheath of a device, or vice versa, it is possible to construct devices within the scope of the present invention so that the features of the marker band were present in the distal portion of the body sheath, and vice versa. Further, while various constructions of various embodiments disclosed herein have been described for devices of certain sizes, it is within the scope of the present invention to construct the various disclosed embodiments in larger or smaller sizes, as appropriate or desired. Further, it may be possible to achieve some or all of the phenomena described in the present disclosure by using forms of radiation other than pulsed radiation, such as continuous wave radiation. The disclosure of pulsed radiation herein should not be understood as limiting the scope of the present invention. It should be understood that while certain beliefs concerning the present invention, its operation, and associated theories are expressed by way of explanation, the invention is not so limited. The invention is entitled to protection within the full scope of the appended claims.

What is claimed is:

1. An apparatus for disrupting occlusive material in a body lumen, comprising:
   an elongated lumen having an intermediate section and a distal section, the intermediate section having at least one opening in a side thereof, and the distal section having an opening at a distal end thereof, the elongated lumen of a construction sufficient to deliver a fluid therethrough to the body lumen; and
   at least one first optical fiber and at least one second optical fiber housed within the elongated lumen, a distal end of the first optical fiber disposed within the distal section, and a distal end of the second optical fiber disposed in a vicinity of the opening of the intermediate section, each of the first and second optical fibers of a construction sufficient to deliver pulsed energy from the distal end thereof to form a bubble in fluid within the body lumen, the pulsed energy from about 100 µJ to about 500 µJ per pulse;

wherein the delivery of energy is sufficient to provide a power of from about 0.5 W to about 2 W and the delivery of fluid is sufficient to avoid substantial thermal damage to the body lumen during the delivery of energy.

2. The apparatus of claim 1, wherein the delivery of fluid is at a rate of from about 0.5 cc/minute to about 3 cc/minute.

3. The apparatus of claim 1, wherein the fluid delivered is a radiation-absorbing fluid.

4. The apparatus of claim 3, wherein the fluid delivered is selected from a group consisting of blood and a dye coolant.

5. The apparatus of claim 3, wherein the fluid delivered is a dye coolant including Indigo Carmine.

6. The apparatus of claim 1, wherein the fluid delivered has an absorption coefficient of from about 170 $cm^{-1}$ to about 300 $cm^{-1}$ for radiation having a wavelength of about 532 nm.

7. The apparatus of claim 1, wherein the fluid delivered has a viscosity of from about 0.5 cP to about 4 cP.

8. The apparatus of claim 1, wherein the energy is in pulses having a duration of from about 5 ns to about 30 ns.

9. The apparatus of claim 1, wherein the energy has a pulse frequency of from about 1 kHz to about 10 kHz.

10. The apparatus of claim 1, wherein the energy has a duty cycle of from about 50% to about 90%.

11. The apparatus of claim 1, wherein the energy has a duty cycle of from about 50% to about 75%.

12. The apparatus of claim 1, wherein the delivery of energy is sufficient to provide an average power of from about 0.5 W to about 1.5 W.

13. The apparatus of claim 1, wherein the energy is delivered in a cycle beginning with the first optical fiber and following with the second optical fiber.

14. The apparatus of claim 1, comprising a plurality of the openings in the intermediate section and a plurality of the second optical fibers, wherein the distal end of each of the second optical fibers is disposed in a vicinity of a corresponding opening in the intermediate section.

15. The apparatus of claim 14, wherein the energy is delivered in a cycle beginning with the first optical fiber and following with each of the second optical fibers in succession.

16. The apparatus of claim 1, wherein a variation in a size of the bubble causes movement of fluid within the body lumen relative to the opening of the intermediate section and the opening of the distal section.

17. The apparatus of claim 1, wherein the delivery of energy causes a net fluid displacement from the opening of the distal section.

18. The apparatus of claim 1, wherein the distal end of the first optical fiber is substantially fixed relative to the distal section.

19. The apparatus of claim 1, wherein the distal end of the second optical fiber is substantially fixed relative to the opening of the intermedi ate section.

20. A method of disrupting occlusive material in a body lumen, comprising:

providing an elongated lumen having an intermediate section and a distal section, the intermediate section having at least one opening in a side thereof, and the distal section having an opening at a distal end thereof;

providing at least one first optical fiber and at least one second optical fiber housed within the elongated lumen, a distal end of the first optical fiber disposed within the distal section, and a distal end of the second optical fiber disposed in a vicinity of the opening of the intermediate section;

delivering pulsed energy from the distal end thereof to form a bubble in a fluid within the body lumen, the energy from about 100 µJ to about 500 µJ per pulse and sufficient to provide a power of from about 0.5 W to about 2 W; and delivering a fluid through the elongated lumen to the body lumen, the delivering of a fluid sufficient to avoid substantial thermal damage to the body lumen during the delivering of energy.

21. The method of claim 20, wherein the delivering of fluid to the body lumen is at a rate of from about 0.5 cc/minute to about 3 cc/minute.

22. The method of claim 20, wherein the fluid being delivered is a radiation-absorbing fluid.

23. The method of claim 22, wherein the fluid being delivered is selected from a group consisting of blood and a dye coolant.

24. The method of claim 22, wherein the fluid being delivered is a dye coolant including Indigo Carmine.

25. The method of claim 20, wherein the fluid being delivered has an absorption coefficient of from about 170 $cm^{-1}$ to about 300 $cm^{-1}$ for radiation having a wavelength of about 532 nm.

26. The method of claim 20, wherein the fluid being delivered has a viscosity of from about 0.5 cP to about 4 cP.

27. The method of claim 20, wherein the energy is in pulses having a duration of from about 5 ns to about 30 ns.

28. The method of claim 20, wherein the energy has a pulse frequency of from about 1 kHz to about 10 kHz.

29. The method of claim 20, wherein the energy has a duty cycle of from about 50% to about 90%.

30. The method of claim 20, wherein the energy has a duty cycle of from about 50% to about 75%.

31. The method of claim 20, wherein the delivery of energy is sufficient to provide an average power of from about 0.5 W to about 1.5 W.

32. The method of claim 20, wherein the energy is delivered in a cycle beginning with the first optical fiber and following with the second optical fiber.

33. The method of claim 20, comprising a plurality of the openings in the intermediate section and a plurality of the second optical fibers, wherein the distal end of each of the second optical fibers is disposed in a vicinity of a corresponding opening in the intermediate section.

34. The method of claim 33, wherein the energy is delivered in a cycle beginning with the first optical fiber and following with each of the second optical fibers in succession.

35. The method of claim 20, wherein a variation in a size of the bubble causes movement of fluid within the body lumen relative to the opening of the intermediate section and the opening of the distal section.

36. The method of claim 20, wherein the delivery of energy causes a net fluid displacement from the opening of the distal section.

37. The method of claim 20, wherein the distal end of the first optical fiber is substantially fixed relative to the distal section.

38. The apparatus of claim 20, wherein the distal end of the second optical fiber is substantially fixed relative to the opening of the intermediate section.

* * * * *